United States Patent
Inoue et al.

(10) Patent No.: US 11,058,742 B2
(45) Date of Patent: Jul. 13, 2021

(54) FOOD COMPOSITION FOR SUPPRESSING HEPATIC LIPOGENESIS

(71) Applicant: FUJI OIL HOLDINGS INC., Osaka (JP)

(72) Inventors: Hiroshi Inoue, Kanazawa (JP); Kumi Kimura, Ishikawa (JP); Nobuhiko Tachibana, Moriya (JP)

(73) Assignee: FUJI OIL HOLDINGS INC., Osaka (JP)

( * ) Notice: Subject to any disclaimer, the term of this patent is extended or adjusted under 35 U.S.C. 154(b) by 0 days.

(21) Appl. No.: 16/797,211

(22) Filed: Feb. 21, 2020

(65) Prior Publication Data
US 2020/0268828 A1 Aug. 27, 2020

(30) Foreign Application Priority Data

Feb. 25, 2019 (JP) .............................. JP2019-031375
Feb. 25, 2019 (JP) .............................. JP2019-031376

(51) Int. Cl.
| | |
|---|---|
| *A61K 38/05* | (2006.01) |
| *A61K 38/16* | (2006.01) |
| *C07K 5/08* | (2006.01) |
| *C07K 5/06* | (2006.01) |
| *A23L 33/18* | (2016.01) |

(52) U.S. Cl.
CPC .............. *A61K 38/05* (2013.01); *A23L 33/18* (2016.08); *A61K 38/16* (2013.01); *A23V 2002/00* (2013.01)

(58) Field of Classification Search
CPC .......... A61K 38/05; A61K 38/16; C07K 5/08; C07K 5/06; C07K 5/06086

USPC ...................... 530/300, 331; 514/21.9, 21.91
See application file for complete search history.

(56) References Cited

U.S. PATENT DOCUMENTS

| | | | |
|---|---|---|---|
| 7,186,425 B2 | 3/2007 | Kohno et al. | |
| 8,871,717 B2* | 10/2014 | Osborne ................ | A61K 38/05 514/18.8 |
| 2004/0014640 A1 | 1/2004 | Kohno et al. | |

FOREIGN PATENT DOCUMENTS

| | | |
|---|---|---|
| JP | 2006-069943 | 3/2006 |
| WO | 02/26243 | 4/2002 |

OTHER PUBLICATIONS

Watanabe et al., "Dietary Mung Bean Protein Reduces Hepatic Steatosis, Fibrosis, and Inflammation in Male Mice with Diet-Induced, Nonalcoholic Fatty Liver Disease", The Journal of Nutrition, 2017, vol. 147, No. 1, pp. 52-60.

* cited by examiner

*Primary Examiner* — Julie Ha
(74) *Attorney, Agent, or Firm* — Wenderoth, Lind & Ponack, L.L.P.

(57) ABSTRACT

A peptide having an effect of suppressing hepatic lipogenesis, where a peptide is one or two or more peptides selected from 11 dipeptides (Ala-Gly, His-Asn, His-Ser, His-Thr, His-Trp, Val-Met, Trp-Glu, Trp-Lys, Tyr-Lys, Tyr-Ser and Tyr-Tyr) and 25 tripeptides (Val-Ile-Leu, Gly-Ser-Leu, Val-Leu-Gln, His-Ala-Gln, Arg-Ala-Val, Lys-Leu-Gly, Ile-Val-Ile, Lys-Pro-Ile, Leu- Val-Ile, Leu-Arg-Asp, Gln-Glu-Glu, Ser-Gly-Glu, Arg-Trp-Phe, Asp-Phe-Phe, Asp-Val-Phe, Pro-Phe-Tyr, Phe-Ile-Arg, Asn-Gly-Arg, Ile-Ile-Pro, Ile-Asp-Arg, Ile-His-Arg, Ile-Asp-Arg, Asn-Arg-Val, Ser-Ser-Val and Val-Phe-Val), is provided. The peptide may be used in a food composition for suppressing hepatic lipogenesis and an agent for suppressing hepatic lipogenesis.

4 Claims, 13 Drawing Sheets

FIG. 32

FOOD COMPOSITION FOR SUPPRESSING HEPATIC LIPOGENESIS

CROSS-REFERENCE TO RELATED APPLICATION

The present application claims the benefits of priority of application No. 2019-31375 and 2019-31376 filed to the Japan Patent Office on Feb. 25, 2019, said applications are incorporated herein by reference in their entirety.

TECHNICAL FIELD

The present invention relates to a peptide having an effect of suppressing hepatic lipogenesis, a food composition and an agent for suppressing hepatic lipogenesis including the peptide, and a method for suppressing hepatic lipogenesis.

BACKGROUND ART

Fatty liver is known to cause a vicious circle with diabetes and cardiovascular disease. An increase in hepatic lipogenesis plays an important role as a trigger of fatty liver, and a lipogenic enzyme is known as a control mechanism thereof.

For the prevention and improvement of fatty liver, it is effective to suppress a hepatic lipogenesis and to enhance a metabolism of lipid in order to suppress the accumulation of lipid.

In recent years, searching various naturally derived functional ingredients have been conducted, and there are reports on ingredients which act on lipid metabolism and can reduce an amount of lipid in the liver. WO 2002/026243 A1 and JP 2006-69943 A disclose that a dried and ground product from a soybean protein or a plant germ has an effect of reducing neutral fat in the blood. However, these documents have not confirmed an effect of suppressing an accumulation of fat in the liver.

In addition, it has been found that an ingestion of vegetable protein improves fatty liver through a suppression of expression of lipogenic enzyme, and that peptide degradation product causes a suppression of lipogenic enzymes in hepatocytes (H. Watanabe et al., "Dietary Mung Bean Protein Reduces Hepatic Steatosis, Fibrosis, and Inflammation in Male Mice with Diet-Induced, Nonalcoholic Fatty Liver Disease", J Nutr. 2017 January; 147(1): 52-60).

The prior arts have not disclosed any ingredient exhibiting an effect of suppressing hepatic lipogenesis.

SUMMARY OF INVENTION

One object of the present invention is to provide an ingredient having an effect of suppressing hepatic lipogenesis. Another object of the present invention is to provide a food composition including an ingredient having an effect of suppressing hepatic lipogenesis. Another object of the present invention is to provide an agent of suppressing hepatic lipogenesis including an ingredient having an effect of suppressing hepatic lipogenesis. Yet another object of the present invention is to provide a method for suppressing hepatic lipogenesis.

The present inventors have intensively studied to solve the above mentioned problems. As a result, they have found that specific dipeptides and tripeptides have an effect of suppressing hepatic lipogenesis. The present invention has been completed by the findings.

That is, the present invention relates to:

(1) a method for suppressing hepatic lipogenesis, including administering an agent for suppressing hepatic lipogenesis including one or more peptide selected from the group consisting of Ala-Gly, His-Asn, His-Ser, His-Thr, His-Trp, Val-Met, Trp-Glu, Trp-Lys, Tyr-Lys, Tyr-Ser, Tyr-Tyr, Val-Ile-Leu, Gly-Ser-Leu, Val-Leu-Gln, His-Ala-Gln, Arg-Ala-Val, Lys-Leu-Gly, Ile-Val-Ile, Lys-Pro-Ile, Leu-Val-Ile, Leu-Arg-Asp, Gln-Glu-Glu, Ser-Gly-Glu, Arg-Trp-Phe, Asp-Phe-Phe, Asp-Val-Phe, Pro-Phe-Tyr, Phe-Ile-Arg, Asn-Gly-Arg, Ile-Ile-Pro, Ile-Asp-Arg, Ile-His-Arg, Ile-Asp-Arg, Asn-Arg-Val, Ser-Ser-Val and Val-Phe-Val, as an active ingredient, to a subject;

(2) the method of (1), where the peptide as an active ingredient is one or more dipeptide selected from the group consisting of Ala-Gly, His-Asn, His-Ser, His-Thr, His-Trp, Val-Met, Trp-Glu, Trp-Lys, Tyr-Lys, Tyr-Ser and Tyr-Tyr; and (3) the method of (1), where the peptide as an active ingredient is one or more tripeptide selected from the group consisting of Val-Ile-Leu, Gly-Ser-Leu, Val-Leu-Gln, His-Ala-Gln, Arg-Ala-Val, Lys-Leu-Gly, Ile-Val-Ile, Lys-Pro-Ile, Leu-Val-Ile, Leu-Arg-Asp, Gln-Glu-Glu, Ser-Gly-Glu, Arg-Trp-Phe, Asp-Phe-Phe, Asp-Val-Phe, Pro-Phe-Tyr, Phe-Ile-Arg, Asn-Gly-Arg, Ile-Ile-Pro, Ile-Asp-Arg, Ile-His-Arg, Ile-Asp-Arg, Asn-Arg-Val, Ser-Ser-Val and Val-Phe-Val.

EFFECT OF INVENTION

In one aspect, the present invention enables to provide a peptide having an effect of suppressing hepatic lipogenesis. In another aspect, the present invention enables to provide a food composition including a specific peptide, having an effect of suppressing hepatic lipogenesis, as an active ingredient. In another aspect, the present invention enables to provide an agent for suppressing hepatic lipogenesis including a specific peptide as an active ingredient. In yet another aspect, the present invention enables to provide a method for suppressing hepatic lipogenesis.

BRIEF DESCRIPTION OF DRAWINGS

FIG. 32 It is a figure showing the results of measuring the Fasn gene expression level in the tertiary screening of 7 tripeptides in the study of tripeptides assumed from the amino acid sequence of α'/β-8S globulin. The black bar graph shows a sample in which the Fasn gene expression level was significantly reduced as compared to the blank (described as Veh).

MODE FOR CARRYING OUT INVENTION

Figure 1:
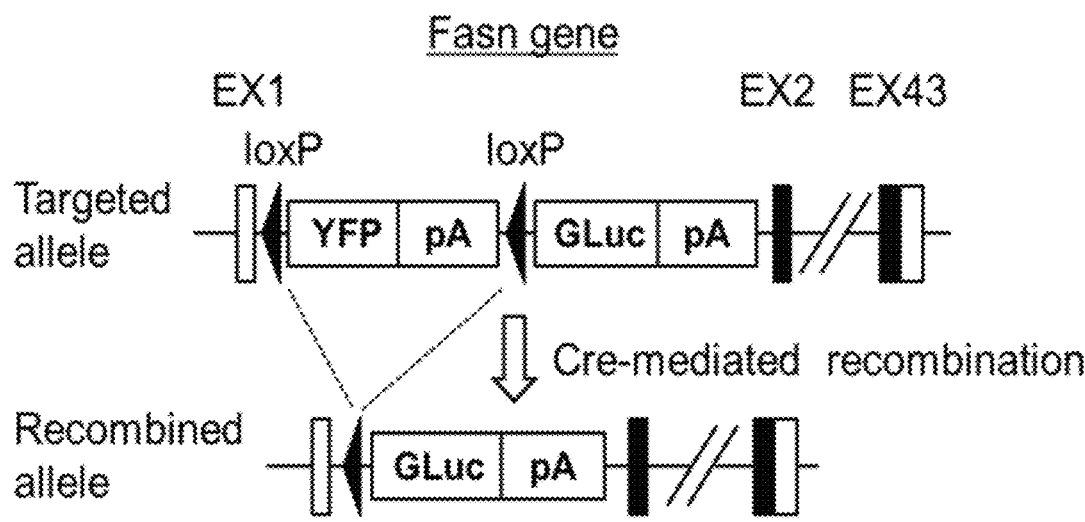
FIG. 1 It is a reference figure of a method of producing Fasn reporter mouse in primary screening.
Figure 2:
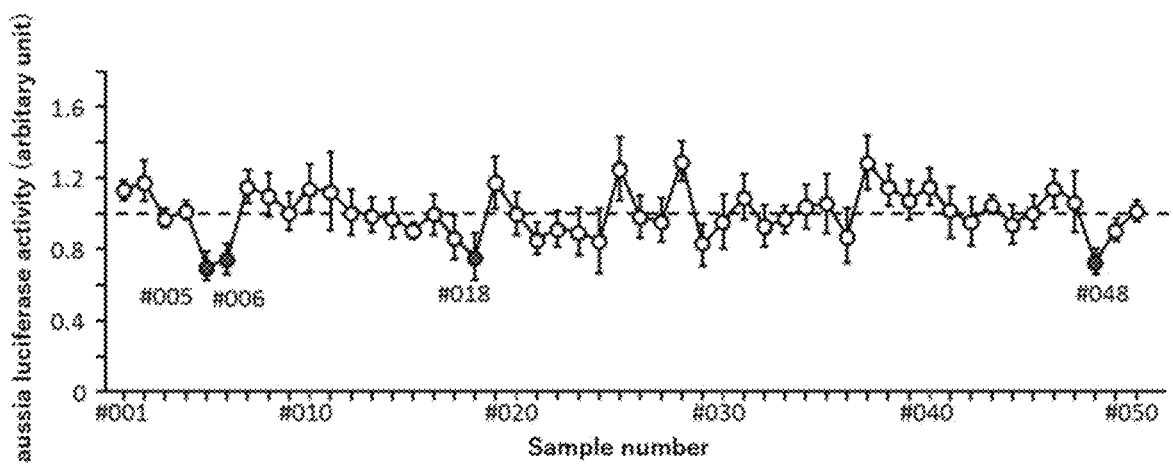
FIG. 2 It is a figure showing the results of measuring the relative activity value of Gaussia luciferase activity with respect to the blank in the primary screening of dipeptides in the dipeptide library (#1-#50). The relative activity value of each sample is indicated by a circle, and a black circle indicates a sample showing a significantly lower value than the blank.
Figure 3:
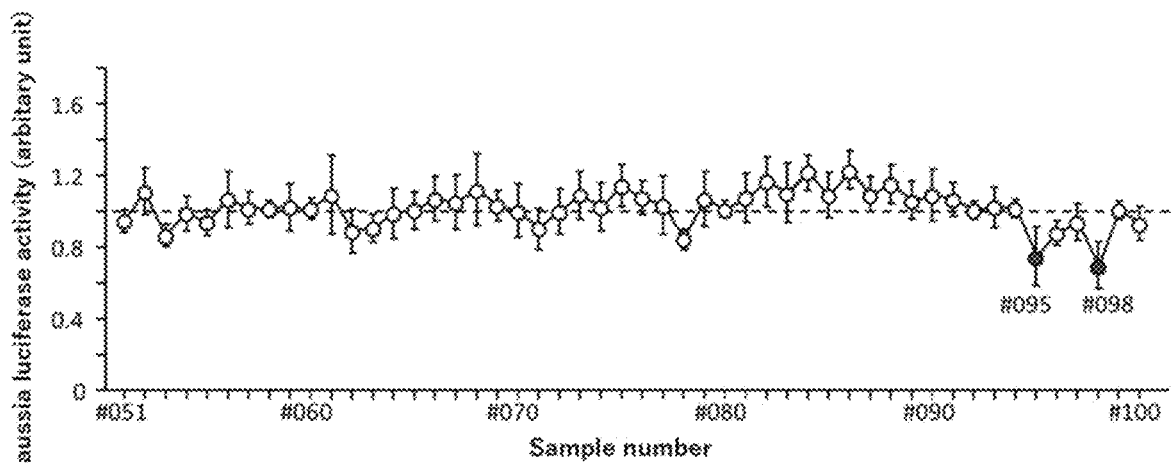
FIG. 3 It is a figure showing the results of measuring the relative activity value of Gaussia luciferase activity with respect to the blank in the primary screening of dipeptides in the dipeptide library (#51-#100). The relative activity value of each sample is indicated by a circle, and a black circle indicates a sample showing a significantly lower value than the blank.
Figure 4:
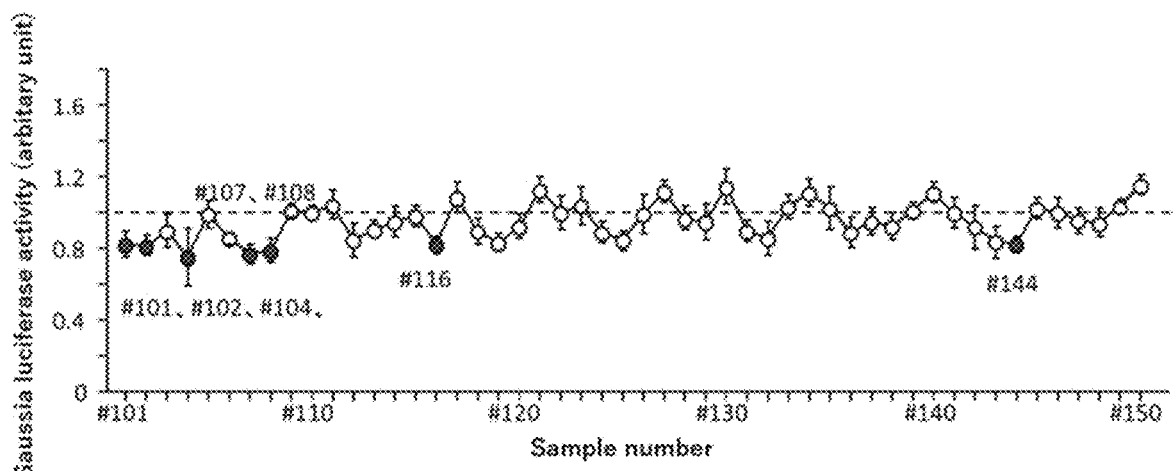
FIG. 4 It is a figure showing the results of measuring the relative activity value of Gaussia luciferase activity with respect to the blank in the primary screening of dipeptides in the dipeptide library (#101-#150). The relative activity value of each sample is indicated by circle, and a black circle indicates a sample showing a significantly lower value than the blank.
Figure 5:
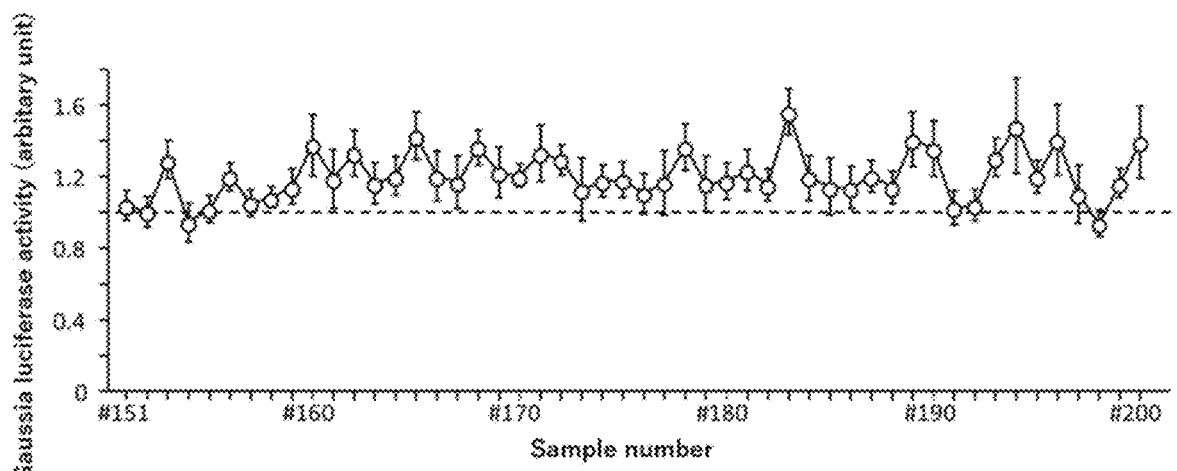
FIG. 5 It is a figure showing the results of measuring the relative activity value of Gaussia luciferase activity with respect to the blank in the primary screening of dipeptides in the dipeptide library (#151-#200). The relative activity value of each sample is indicated by a circle, and a black circle indicates a sample showing a significantly lower value than the blank.
Figure 6:
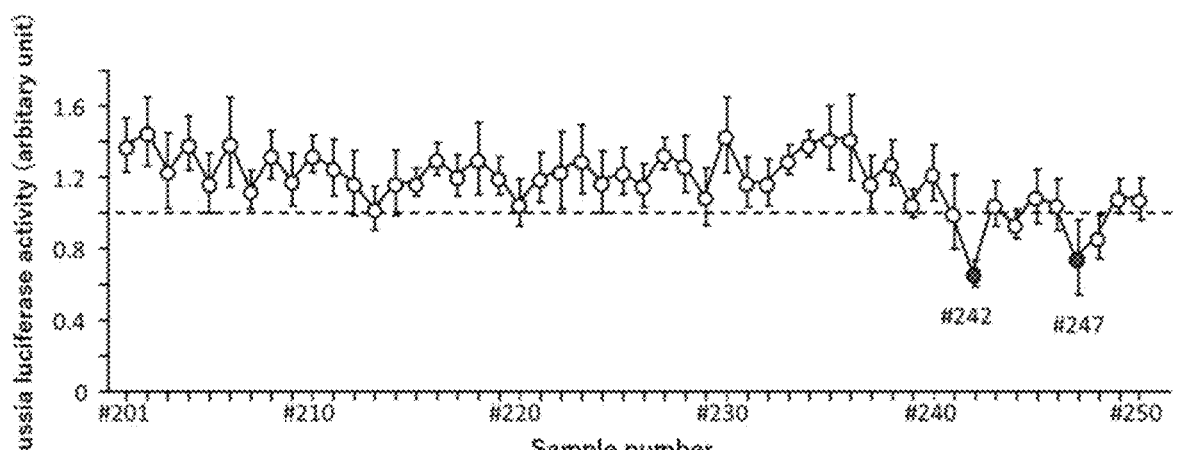
FIG. 6 It is a figure showing the results of measuring the relative activity value of Gaussia luciferase activity with respect to the blank in the primary screening of dipeptides in the dipeptide library (#201-#250). The relative activity value of each sample is indicated by a circle, and a black circle indicates a sample showing a significantly lower value than the blank.
Figure 7:
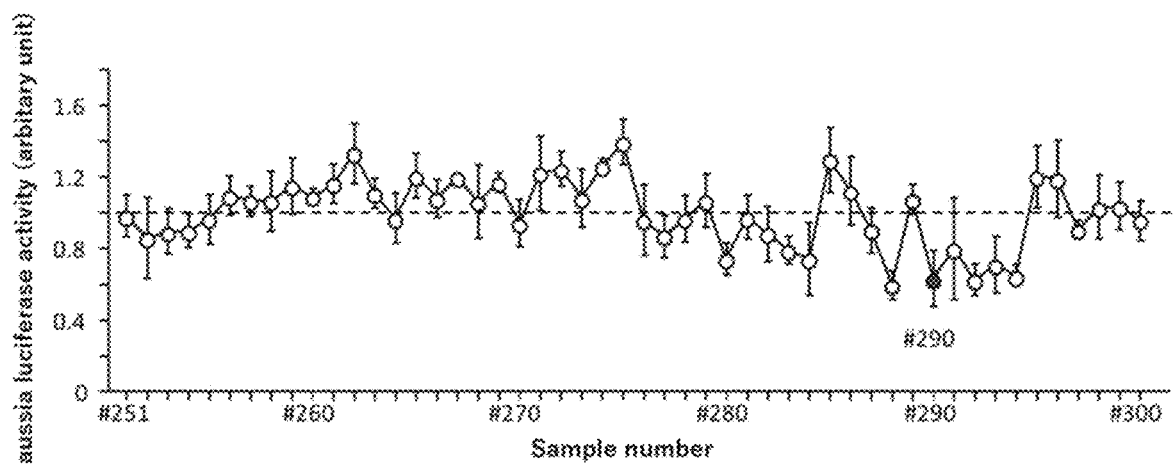
FIG. 7 It is a figure showing the results of measuring the relative activity value of Gaussia luciferase activity with respect to the blank in the primary screening of dipeptides in the dipeptide library (#251-#300). The relative activity value of each sample is indicated by a circle, and a black circle indicates a sample showing a significantly lower value than the blank.
Figure 8:
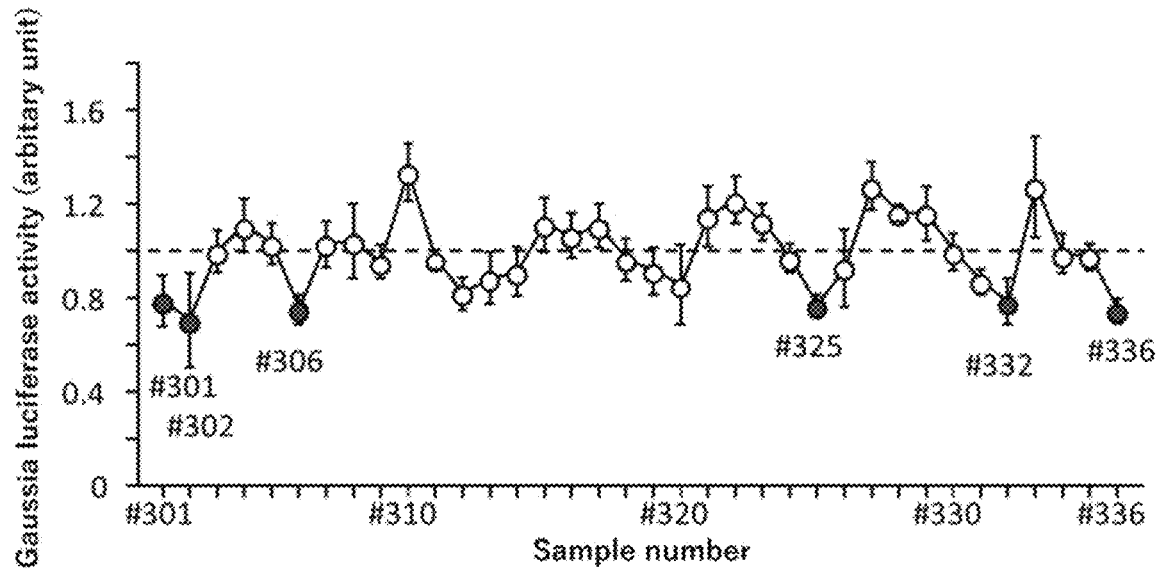
FIG. 8 It is a figure showing the results of measuring the relative activity value of Gaussia luciferase activity with respect to the blank in the primary screening of dipeptides in the dipeptide library (#301-#336). The relative activity value of each sample is indicated by a circle, and a black circle indicates a sample showing a significantly lower value than the blank.

As used herein, the term "about" refers to a range of ±10%, preferably ±5%. Numerical values that are the boundary values of the range are considered to be described herein.

(Peptide Having an Effect of Suppressing Hepatic Lipogenesis)

In one aspect, the present invention provides a peptide having an effect of suppressing hepatic lipogenesis. More specifically, a peptide of this aspect is one or two or more peptides selected from 11 dipeptides (Ala-Gly, His-Asn, His-Ser, His-Thr, His-Trp, Val-Met, Trp-Glu, Trp-Lys, Tyr-Lys, Tyr-Ser and Tyr-Tyr) and 25 tripeptides (Val-Ile-Leu, Gly-Ser-Leu, Val-Leu-Gln, His-Ala-Gln, Arg-Ala-Val, Lys-Leu-Gly, Ile-Val-Ile, Lys-Pro-Ile, Leu-Val-Ile, Leu-Arg-Asp, Gln-Glu-Glu, Ser-Gly-Glu, Arg-Trp-Phe, Asp-Phe-Phe, Asp-Val-Phe, Pro-Phe-Tyr, Phe-Ile-Arg, Asn-Gly-Arg, Ile-Ile-Pro, Ile-Asp-Arg, Ile-His-Arg, Ile-Asp-Arg, Asn-Arg-Val, Ser-Ser-Val and Val-Phe-Val). In one embodiment, the peptide of this aspect consists of one or more dipeptide. In another embodiment, the peptide of this aspect consists of one or more tripeptide. In other embodiment, the peptide of this aspect is a mixture of one or more dipeptide and one or more tripeptide.

As used herein, the above dipeptides and tripeptides may be represented by using one-letter abbreviations of amino acids as follows.

Ala-Gly:AG, His-Asn:HN, His-Ser:HS, His-Thr:HT, His-Trp:HW, Val-Met:VM, Trp-Glu:WE, Trp-Lys:WK, Tyr-Lys:YK, Tyr-Ser:YS, Tyr-Tyr:YY, Val-Ile-Leu:VIL, Gly-Ser-Leu:GSL, Val-Leu-Gln:VLQ, His-Ala-Gln:HAQ, Arg-Ala-Val:RAV, Lys-Leu-Gly:KLG, Ile-Val-Ile:IVI, Lys-Pro-Ile:KPI, Leu-Val-Ile:LVI, Leu-Arg-Asp:LRD, Gln-Glu-Glu:QEE, Ser-Gly-Glu:SGE, Arg-Trp-Phe:RWF, Asp-Phe-Phe:DFF, Asp-Val-Phe:DVF, Pro-Phe-Tyr:PFY, Phe-Ile-Arg:FIR, Asn-Gly-Arg:NGR, Ile-Ile-Pro:IIP, Ile-Asp-Arg:IDR, Ile-His-Arg:IHR, Ile-Asp-Arg:IDR, Asn-Arg-Val:NRV, Ser-Ser-Val:SSV, Val-Phe-Val:VFV.

As a mechanism by which the peptide of this aspect exerts an action of suppressing hepatic lipogenesis, it is assumed by suppressing an expression of mRNA of fatty acid synthase (FAS) (mRNA (Fasn)), which is an enzyme of synthesizing fatty acids in hepatic de novo lipogenesis.

For example, an effect of suppressing hepatic lipogenesis may be confirmed by the method described in "(Secondary Screening Method)" below. In this case, when the amount of mRNA (Fasn) in the group of adding a peptide is significantly lower than that in the group without adding the peptide in this method, the peptide is confirmed as having an effect of suppressing hepatic lipogenesis.

The peptide of this aspect may be synthesized from amino acids or may be obtained by hydrolyzing a protein. Means for hydrolyzing a protein include hydrolysis with a protease, hydrolysis with an acid, and hydrolysis with an alkali. Hydrolysis with a protease is preferred. In one embodiment, the peptide of this aspect is synthetic peptide. In another embodiment, the peptide of this aspect is a peptide obtained by hydrolyzing a protein. In more specific embodiment, the peptide of this aspect is a peptide obtained by hydrolyzing a protein with a protease.

As a raw material of the peptide, any protein such as vegetable protein and animal protein may be used. Examples of a raw material of the vegetable protein include bean such as soybean, pea, mung bean and chickpea; grain such as rice, corn and wheat; and nut such as almond, cashew nut, walnut, pistachio, hazelnut and macadamia nut, and examples of a raw material of animal protein include beef, pork, chicken, egg and milk. Specific examples of the raw material of the peptide include bean-derived protein such as soybean, pea, mung bean, and chickpea, and more specific examples include mung bean-derived protein.

(Protease)

In the case of protein hydrolysis by a protease, protease treatment is performed to a slurry or aqueous solution of the above-described protein as a substrate. Protease used in the treatment may be selected from any proteases, such as "metalloprotease", "acid protease", "thiol protease" and "serine protease", in the classification of proteases, preferably selected from proteases classified into "metal protease", "thiol protease" or "serine protease", regardless of animal-, plant- or microorganism-origin.

This classification of protease is normally carried out in the field of enzyme science, i.e. a method of classification according to the kind of amino acid in the active center. As typical examples of each enzyme, "metalloprotease" includes *Bacillus*-derived neutral protease, *Streptomyces*-derived neutral protease, *Aspergillus*-derived neutral protease, and "Thermoase"; "acid protease" includes pepsin, *Aspergillus*-derived acid protease, and "Sumizyme AP"; "thiol protease" includes bromelain, and papain; and "serine protease" includes trypsin, chymotrypsin, subtilisin, *Streptomyces*-derived alkaline protease, "Alcalase", and "Bioprase". The classification of other enzymes may be confirmed by the working pH and reactivity with inhibitors. Enzymes having different active center enable to obtain an enzymatic degradation product effectively because the active site to a substrate is very different between such enzymes and "uncut portions" are reduced.

Reaction pH and reaction temperature of the protease treatment may be set to match the characteristics of the protease used. Usually, a reaction may be carried out at near the optimum pH and near the optimum temperature. Generally, the reaction temperature is 20 to 80° C., preferably 40 to 60° C. After the reaction, the residual enzyme activity is inactivated by heating to a sufficient temperature (about 60 to 170° C.) to deactivate the enzyme.

The reaction solution after the protease treatment may be used directly or after concentrated. Typically, the solution is used in powder form after sterilization, splay-drying, or freeze-drying. Heat sterilization is preferred as the sterilization. And the heating temperature is preferably 110 to 170° C., more preferably 130 to 170° C., and the heating time is preferably 3 to 20 seconds. In addition, the reaction solution may be adjusted to any pH, and a precipitates and a suspension generated during pH adjustment may also be removed by means such as centrifugation and filtration. Further, it may be purified by an activated carbon or an adsorption resin.

(Hydrolysis with Acid or Alkali)

Conditions such as substrate concentration, amount of enzyme, treatment temperature, pH and time in protein hydrolysis with acid or alkali may be appropriately set.

The peptide of this aspect may be used for a manufacture of a food composition for suppressing hepatic lipogenesis. In addition, the peptide of this aspect may be used for a manufacture of an agent for suppressing hepatic lipogenesis.

(Food Composition for Suppressing Hepatic Lipogenesis)

In one aspect, the present invention provides a food composition for suppressing hepatic lipogenesis including a peptide described in the aspect of "(peptide having an effect of suppressing hepatic lipogenesis)" above. More specifically, a food composition for suppressing hepatic lipogenesis of this aspect includes one or two or more peptides selected from 11 dipeptides (Ala-Gly, His-Asn, His-Ser, His-Thr, His-Trp, Val-Met, Trp-Glu, Trp-Lys, Tyr-Lys, Tyr-Ser and Tyr-Tyr) and 25 tripeptides (Val-Ile-Leu, Gly-Ser-Leu, Val-Leu-Gln, His-Ala-Gln, Arg-Ala-Val, Lys-Leu-Gly, Ile-Val-Ile, Lys-Pro-Ile, Leu-Val-Ile, Leu-Arg-Asp, Gln-Glu-Glu, Ser-Gly-Glu, Arg-Trp-Phe, Asp-Phe-Phe, Asp-Val-Phe, Pro-Phe-Tyr, Phe-Ile-Arg, Asn-Gly-Arg, Ile-Ile-Pro, Ile-Asp-Arg, Ile-His-Arg, Ile-Asp-Arg, Asn-Arg-Val, Ser-Ser-Val and Val-Phe-Val) as an active ingredient. In one embodiment, the peptide included in the food composition for suppressing hepatic lipogenesis of this aspect consists of one or more dipeptide. In another embodiment, the peptide included in the food composition for suppressing hepatic lipogenesis of this aspect consists of one or more tripeptide. In other embodiment, the peptide included in the food composition for suppressing hepatic lipogenesis of this aspect is a mixture of one or more dipeptide and one or more tripeptide.

The food composition for suppressing hepatic lipogenesis of this aspect may be produced in a form of supplement, a form of food additive, or a form added to a food, using only the above-described peptide or, if necessary, mixing with another raw material as appropriate. In the form of supplement, it may be used in various form such as liquid, powder, granule, pill, tablet and capsule. In the form of food additive, it may be used in various form such as liquid, paste, gel, powder, granule and solid. In the form added to a food, it may be a form of a solid food such as biscuit, cake, bread, food bar and meat product, a form of a drink by dissolved into water, or a fluid or semi-solid food such as yogurt, pudding and jelly. The other raw material mixed in the food composition of the present aspect is not particularly limited as long as it can be used as a food additive or a food. Examples of the other raw material include seasoning such as vinegar, miso, soy sauce and amino acid; acidulant such as acetic acid, citric acid, malic acid and lactic acid; sweetener such as aspartame, sucralose, acesulfame potassium and stevia extract; bittering agent; spice; preservative; coloring agent; flavor; salt; sugar such as glucose, fructose, sucrose and lactose; fat; antioxidant; vitamin; mineral; stabilizer; thickener; bulking agent; gelling agent such as pectin, gellan gum, agar and gelatin; and excipient such as lactose, starch, dextrin and cellulose. In a more specific embodiment, the food composition of this aspect is in the form of a supplement. More specific examples of the supplement include a supplement as a capsule including only the above-described peptide in a capsule, a supplement as a powder or granulated formulation obtained by adding an excipient to the above-described peptide, a supplement as a tablet obtained by adding an excipient to the above-described peptide and compressing to a tablet form, and a supplement as jelly in which the above-described peptide and a gelling agent are packed in a pouch.

A content of the peptide in the food composition for suppressing hepatic lipogenesis of this aspect is not particularly limited, for example, may be about 0.1, 0.2, 0.3, 0.5, 0.7, 1, 1.2, 1.5, 1.7, 2, 2.5, 3, 3.5, 4, 4.5, 5, 7, 9, 10, 12, 15, 20, 25, 30, 35, 40, 45, 50, 55, 60, 65, 70, 75, 80, 85, 90, 92, 95, 97, 98, 99, 100% by weight with respect to the food composition. In addition, the content may be in an arbitrary range having any of these values as an upper limit and a lower limit. Further, an intake amount of the food composition for suppressing hepatic lipogenesis of this aspect is not particularly limited. For example, the intake amount of the peptide in the food composition may be about 0.001 to 100 mg/kg body weight per one time, for example, about 0.01 to 50 mg/kg body weight, 0.1 to 25 mg/kg body weight or about 0.5 to 10 mg/kg body weight per one time.

(Agent for Suppressing Hepatic Lipogenesis)

In one aspect, the present invention provides an agent for suppressing hepatic lipogenesis including the peptide described in the aspect of "(peptide having an effect of suppressing hepatic lipogenesis)" above. More specifically, an agent for suppressing hepatic lipogenesis of this aspect includes one or two or more peptides selected from 11 dipeptides (Ala-Gly, His-Asn, His-Ser, His-Thr, His-Trp, Val-Met, Trp-Glu, Trp-Lys, Tyr-Lys, Tyr-Ser and Tyr-Tyr) and 25 tripeptides (Val-Ile-Leu, Gly-Ser-Leu, Val-Leu-Gln, His-Ala-Gln, Arg-Ala-Val, Lys-Leu-Gly, Ile-Val-Ile, Lys-Pro-Ile, Leu-Val-Ile, Leu-Arg-Asp, Gln-Glu-Glu, Ser-Gly-Glu, Arg-Trp-Phe, Asp-Phe-Phe, Asp-Val-Phe, Pro-Phe-Tyr, Phe-Ile-Arg, Asn-Gly-Arg, Ile-Ile-Pro, Ile-Asp-Arg, Ile-His-Arg, Ile-Asp-Arg, Asn-Arg-Val, Ser-Ser-Val and Val-Phe-Val) as an active ingredient. In one embodiment, the peptide included in the agent for suppressing hepatic lipogenesis of this aspect consists of one or more dipeptide. In another embodiment, the peptide included in the agent for suppressing hepatic lipogenesis of this aspect consists of one or more tripeptide. In other embodiment, the peptide included in the agent for suppressing hepatic lipogenesis of this aspect is a mixture of one or more dipeptide and one or more tripeptide.

The agent for suppressing hepatic lipogenesis of this aspect may be produced using only the above-described peptide or, if necessary, mixing with another raw material as appropriate. Typically, the agent for suppressing hepatic lipogenesis of this aspect may be a pharmaceutical composition.

A dosage form of the agent for suppressing hepatic lipogenesis of this aspect is not particularly limited, and for example, an agent for oral administration such as granule, fine granule and tablet; injectable preparation such as liquid preparation and dissolving powder before use; transdermal preparation such as ointment, liquid preparation, cream and gel; and suppository.

An administration route of the agent for suppressing hepatic lipogenesis of this aspect is not particularly limited, and examples thereof include oral administration, intravenous administration, intramuscular administration, local administration, transdermal administration and rectal administration. An example of more specific administration route is oral administration.

The agent for suppressing hepatic lipogenesis of this aspect may include, in addition to the peptide as an active ingredient, another pharmaceutically acceptable raw material such as pharmaceutically acceptable carrier, excipient, diluent, isotonic agent, additive, disintegrant, binder, stabilizer, coating, dispersion media, bulking agent, pH buffer, lubricant, glidant, flavor, sweetener, solubilizer, solvent, gelling agent and nutrient. The other raw material may affect an absorption and blood concentration and may cause changes in pharmacokinetics of the agent for suppressing hepatic lipogenesis of this aspect. Specific examples of the other raw material include water, saline, animal fat, vegetable fat, lactose, starch, gelatin, crystalline cellulose, gum, talc, magnesium stearate, hydroxypropylcellulose, polyalkylene glycol, polyvinyl alcohol and glycerin.

A content of the peptide in the agent for suppressing hepatic lipogenesis of this aspect is not particularly limited, for example, may be about 0.1, 0.2, 0.3, 0.5, 0.7, 1, 1.2, 1.5, 1.7, 2, 2.5, 3, 3.5, 4, 4.5, 5, 7, 9, 10, 12, 15, 20, 25, 30, 35, 40, 45, 50, 55, 60, 65, 70, 75, 80, 85, 90, 92, 95, 97, 98, 99, 100% by weight with respect to the agent. In addition, the content may be in an arbitrary range having any of these values as an upper limit and a lower limit. Further, an administration amount of the agent for suppressing hepatic lipogenesis of this aspect is not particularly limited. For example, the administration amount of the peptide in the agent may be about 0.001 to 100 mg/kg body weight per one dose, for example, about 0.01 to 50 mg/kg body weight, 0.1 to 25 mg/kg body weight or about 0.5 to 10 mg/kg body weight per one dose.

An administration frequency of the agent for suppressing hepatic lipogenesis of this aspect is not particularly limited. Examples of the administration frequency include administration once to plural times, for example, 2, 3, 4 or 5 times, a day and continuous administration by infusion.

(Method for Suppressing Hepatic Lipogenesis)

In one aspect, the present invention provides a method for suppressing hepatic lipogenesis in a subject by ingesting the above food composition for suppressing hepatic lipogenesis or administering the above agent for suppressing hepatic lipogenesis.

As used herein, "subject" includes human or non-human animal, and examples of the animal may include, but not limited to, human, mouse, rat, monkey, pig, dog, dog, rabbit, hamster, and guinea pig.

In one embodiment, the "subject" in this aspect is a subject in need of suppression of hepatic lipogenesis. More specifically, examples of diseases requiring suppression of hepatic lipogenesis include obesity, fatty liver, steatohepatitis, cirrhosis, diabetes, cardiomyopathy and arteriosclerosis. That is, in another embodiment, the method of this aspect provides a method of treating or preventing a disease requiring a suppression of hepatic lipogenesis.

In another embodiments, the method of this aspect further includes administering a pharmaceutical composition for treating or preventing a disease such as obesity, fatty liver, steatohepatitis, cirrhosis, diabetes, cardiomyopathy and arteriosclerosis. In one embodiment, the food composition or agent for suppressing hepatic lipogenesis and the pharmaceutical composition are administered concurrently. In another embodiment, the food composition or agent for suppressing hepatic lipogenesis is administered after administration of the pharmaceutical composition. In yet another embodiment, the pharmaceutical composition is administered after administration of the food composition or agent for suppressing hepatic lipogenesis.

All disclosures in the aspects of the "food composition for suppressing hepatic lipogenesis" and the "agent for suppressing hepatic lipogenesis", for example, definition of form or dosage form, intake amount or administration amount etc.; are applied to the method of this aspect.

EXAMPLES

Hereinafter, the present invention will be described by Examples. In addition, % in Examples is volume basis unless otherwise noticed.

(Feeding Procedure of Mouse)

The mouse for collecting hepatocyte is illuminated by a 12-hour light/dark cycle, and is bred under a constant temperature environment with free drinking and free feeding. Eight to 12 week old mouse is harvested for hepatocyte by collagenase perfusion under anesthesia under pentobarbital and isoflurane. A reporter mouse is prepared as described below. And, a C57BL/6J mouse without a transgene purchased from Japan SLC, Inc. is used as a wild-type mouse.

(Primary Screening Method)

In primary screening, an expression of Fasn (Fatty acid synthase) gene, which is fatty acid synthase gene, is evaluated by measuring Fasn promoter activity using Fasn gene-introduced reporter mouse-derived cultured hepatocyte in order to roughly confirm whether a peptide has an effect of suppressing hepatic lipogenesis. More specifically, the method includes steps such as Preparation of Hepatic Fasn Reporter Mouse and Evaluation. Details of the method are shown below.

(Preparation of Hepatic Fasn Reporter Mouse)

DNA for introducing into mouse is prepared by inserting genome cassette containing yellow fluorescent protein (YFP) having loxP sequences (34 bp DNA sequence derived from the bacteriophage P1 genome) at both ends and poly-A chain, followed by Gaussia luciferase (GLuc) and poly-A chain, to immediately after Fasn gene promoter of a full-length 240.2 kb DNA containing Fasn locus. The prepared DNA is introduced into a fertilized egg harvested from a C57BL/6J mouse to produce mouse A. A progeny, obtained by crossing mouse A with C57BL/6J mouse, is crossed with mouse B into which rat albumin promoter and Cre recombinase are introduced, and a mouse having both mouse A and mouse B genes is produced as a reporter mouse. In this reporter mouse, the gene cassette containing YFP and poly-A chain is removed liver tissue-specifically by Cre recombinase, which is expressed liver-specifically by rat albumin promoter, to obtain liver-tissue specific expression of Gluc by the Fasn gene promoter (FIG. 1). The Fasn gene promoter causes an increase in the expression and activity of Gaussia luciferase (GLuc) in association with the expression of fatty acid synthase in the liver.

(Evaluation)

Hepatocyte isolated from hepatic Fasn reporter mouse is cultured in a 96-well plate in Dulbecco's modified Eagle's medium (DMEM) containing 1% penicillin and streptomycin and 10% fetal calf serum (FCS) for 8 hours, and then subjected to 16 hours starvation by replacing the medium with Dulbecco's modified Eagle's medium (DMEM) containing 1% penicillin and streptomycin. The medium is recovered and cultured for 24 hours in a medium containing insulin, liver X receptor (LXR) agonist, amino acid mixture, and each peptide (100 µg/ml in the medium). In addition, as a group without adding peptide, a sample to which 10% dimethyl sulfoxide (DMSO) is added instead of the peptide is similarly cultured for 24 hours. A promoter that promotes the expression of the Fasn gene involved in fatty acid synthesis is activated by culturing with adding insulin, LXR agonist, and amino acid mixture to the medium. When the promoter is activated, Gaussia luciferase (GLuc) gene is expressed, and the activity of Gaussia luciferase (GLuc) is measured. The activity of Gaussia luciferase is measured by a luminometer LB941 (Berthold Technologies Gmbh & Co. KG) using coelenterazine as a luminescent substrate and according to the method described in Biochem. Biophys. Res. Commun. 365, 96-101 (2007). The measured value of the group adding peptide and the measured value of the group adding 10% DMSO only (group without adding peptide) are measured, and the relative activity of the group adding peptide as compared to the measured value of the group without adding peptide, which is defined as 1, is determined and evaluated. The significance test is carried out using the statistical analysis software "StatView" (SAS Institute Inc.) and the result is evaluated using the Bonferroni method as a comparison with the control.

(Secondary Screening Method)

In the secondary screening, evaluation is performed by measuring the expression level of Fasn gene mRNA using isolated hepatocyte derived from wild-type mouse (C57BL/6J mouse). More specifically, isolated hepatocyte derived from wild-type mouse (C57BL/6J mouse) is plated in 12-well plate in Dulbecco's modified Eagle's medium (DMEM) containing 1% penicillin and streptomycin, and 10% fetal calf serum (FCS) for 8 hours, and then subjected to 16 hours starvation by replacing the medium with Dulbecco's modified Eagle's medium (DMEM) containing 1% penicillin and streptomycin. The medium is recovered and cultured for 24 hours in a medium containing insulin, liver X receptor (LXR) agonist, amino acid mixture, and each peptide (100 µg/ml in the medium at final concentration). In addition, as a group without adding peptide, a sample to which 10% dimethyl sulfoxide (DMSO) is added instead of the peptide is similarly cultured for 24 hours. After removing the medium from each well, mRNA is extracted. The extraction of mRNA is performed with the SV Total RNA Isolation System (Promega, Z3105), reverse transcription from the RNA is performed with the PrimeScript RT reagent kit (Takara, RR0037A), and quantitative PCR is performed with the CFX384 Real-Time System and C1000 Thermal Cycler using the SYBR Select Master Mix kit (Life technologies, 4472908). The methods comply with the instructions for the kit and equipment.

(Tertiary Screening Method)

The amount of peptide to be added is changed (as used herein, the final concentration of the sample is 10, 30, 100 µg/ml, unless otherwise specified), and the expression level of the Fasn gene is evaluated in the same manner as in the secondary screening.

Example 1: Dipeptide (Primary Screening)

Dipeptides which may be involved in an effect of suppressing hepatic lipogenesis were screened from 336 dipeptides library (AnaSpec, Inc.). Screening was carried out according to the method of the above-mentioned "(Primary Screening Method)". The results are shown in FIGS. 2 to 8.

Statistically, 22 dipeptides were confirmed as having an activity of suppressing Gaussia luciferase activity (FIGS. 2-8, Table 1). Therefore, in order to confirm in detail whether these 22 peptides were actually effective, these peptides were synthesized and subjected to secondary screening.

TABLE 1

22 dipeptides confirmed to be effective in primary screening

| Dipeptide library No. | Dipeptide |
| --- | --- |
| #005 | Ala-Gly (AG) |
| #006 | Ala-His (AH) |
| #018 | Ala-Tyr (AY) |
| #048 | Glu-Arg (ER) |
| #095 | His-Lys (HK) |
| #098 | His-Asn (HN) |
| #101 | His-Ser (HS) |
| #102 | His-Thr (HT) |
| #104 | His-Trp (HW) |
| #107 | Ile-Asp (ID) |
| #108 | Ile-Glu (IE) |
| #116 | Ile-Pro (IP) |
| #144 | Leu-Glu (LE) |
| #242 | Arg-Val (RV) |

TABLE 1-continued 22 dipeptides confirmed to be effective in primary screening

| Dipeptide library No. | Dipeptide |
|---|---|
| #247 | Ser-Phe (SF) |
| #290 | Val-Met (VM) |
| #301 | Trp-Glu (WE) |
| #302 | Trp-Phe (WF) |
| #306 | Trp-Lys (WK) |
| #325 | Tyr-Lys (YK) |
| #332 | Tyr-Ser (YS) |
| #336 | Tyr-Tyr (YY) |

(Secondary Screening)

Figure 9:
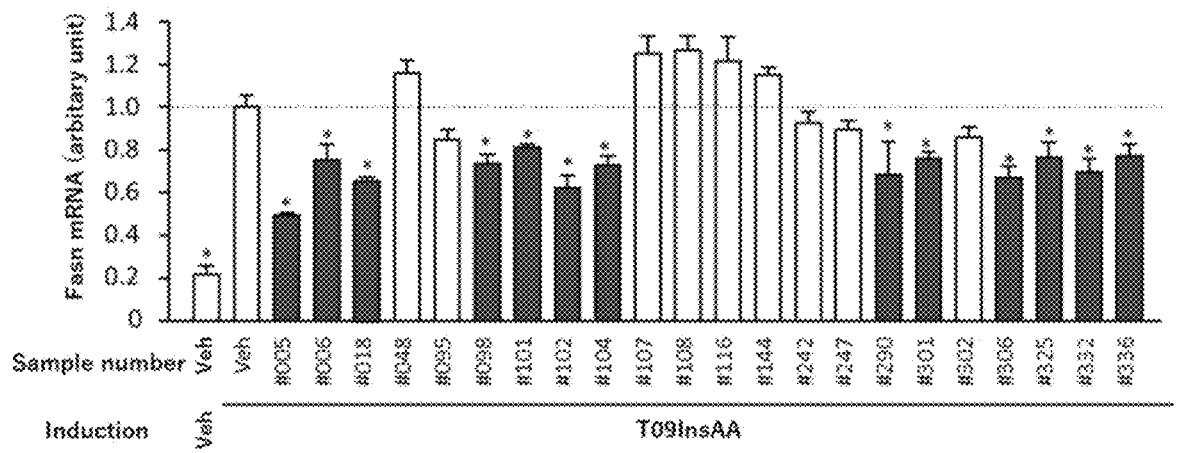
FIG. 9 It is a figure showing the results of measuring the Fasn gene expression level in the secondary screening of 22 dipeptides. The black bar graph shows a sample in which the Fasn gene expression level was significantly reduced as compared to the blank (described as Veh).

Dipepitdes shown in Table 1 were synthesized by peptide synthesizer (ResPep SL (INTAVIS Bioanalytical Instruments AG)) owned by Fuji Oil Co. Ltd. The synthesized dipeptides were evaluated by the method according to the above-described "(Secondary Screening Method)". The results are shown in FIG. 9.

Among the 22 dipeptides, 13 dipeptides, Ala-Gly, Ala-His, Ala-Tyr, His-Asn, His-Ser, His-Thr, His-Trp, Val-Met, Trp-Glu, Trp-Lys, Tyr-Lys, Tyr-Ser and Tyr-Tyr, significantly suppressed the expression of the Fasn gene with respect to the control.

(Tertiary Screening)

Figure 10:
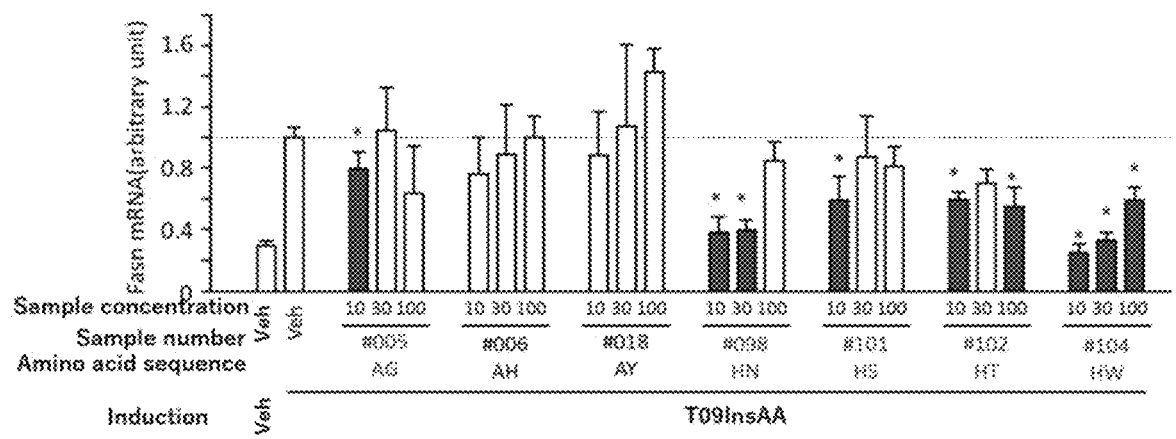
FIG. 10 It is a figure showing the results of measuring the Fasn gene expression level in the tertiary screening of 11 dipeptides. The black bar graph shows a sample in which the Fasn gene expression level was significantly reduced as compared to the blank (described as Veh).
Figure 11:
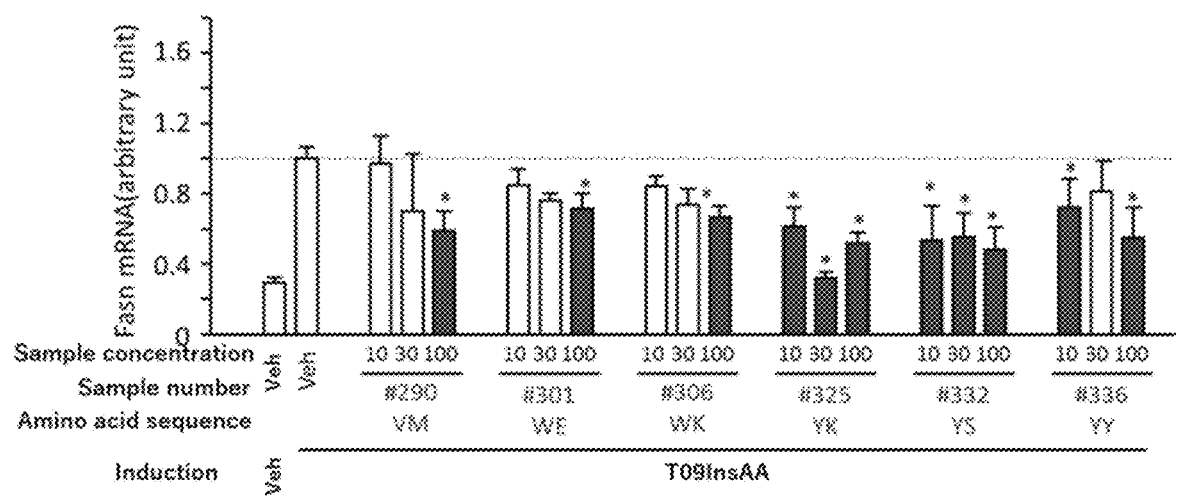
FIG. 11 It is a figure showing the results of measuring the Fasn gene expression level in the tertiary screening of 11 dipeptides. The black bar graph shows a sample in which the Fasn gene expression level was significantly reduced as compared to the blank (described as Veh).
Figure 12:
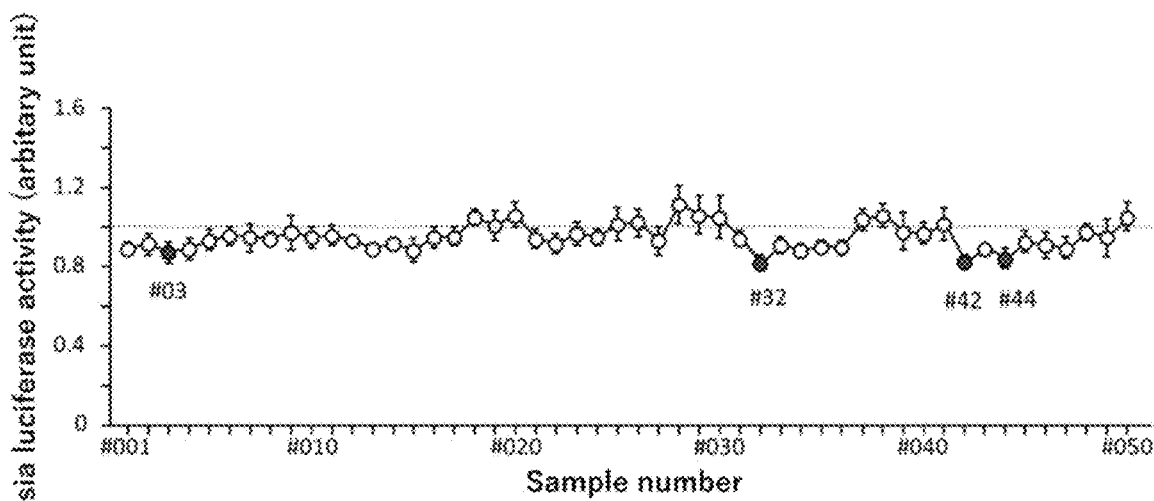
FIG. 12 It is a figure showing the results of measuring the relative activity value of Gaussia luciferase activity with respect to the blank in the primary screening of tripeptides in the tripeptide library (#1-#50) assumed from the amino acid sequence of α-8S globulin. The relative activity value of each sample is indicated by a circle, and a black circle indicates a sample showing a significantly lower value than the blank.
Figure 13:
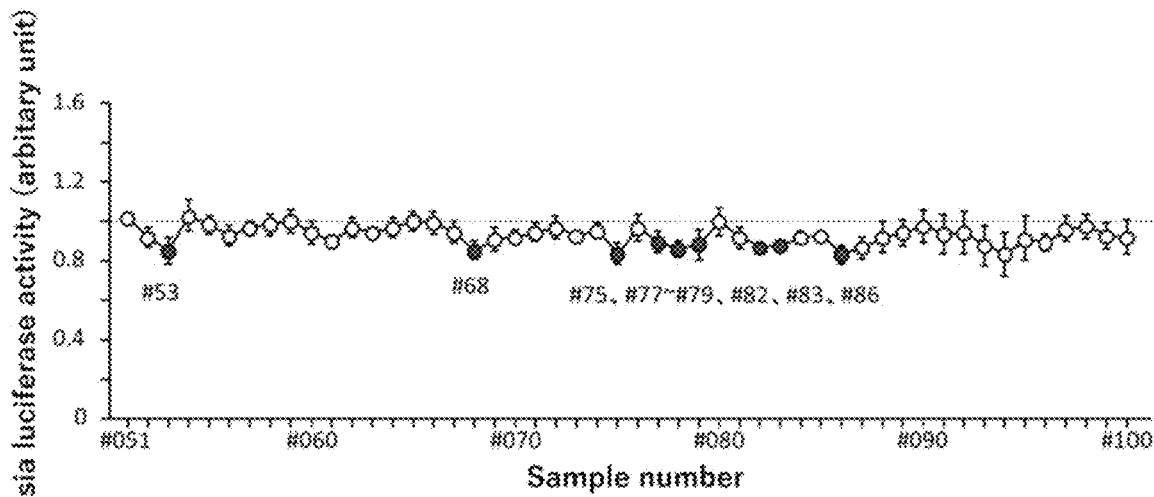
FIG. 13 It is a figure showing the results of measuring the relative activity value of Gaussia luciferase activity with respect to the blank in the primary screening of tripeptides in the tripeptide library (#51-#100) assumed from the amino acid sequence of α-8S globulin. The relative activity value of each sample is indicated by a circle, and a black circle indicates a sample showing a significantly lower value than the blank.
Figure 14:
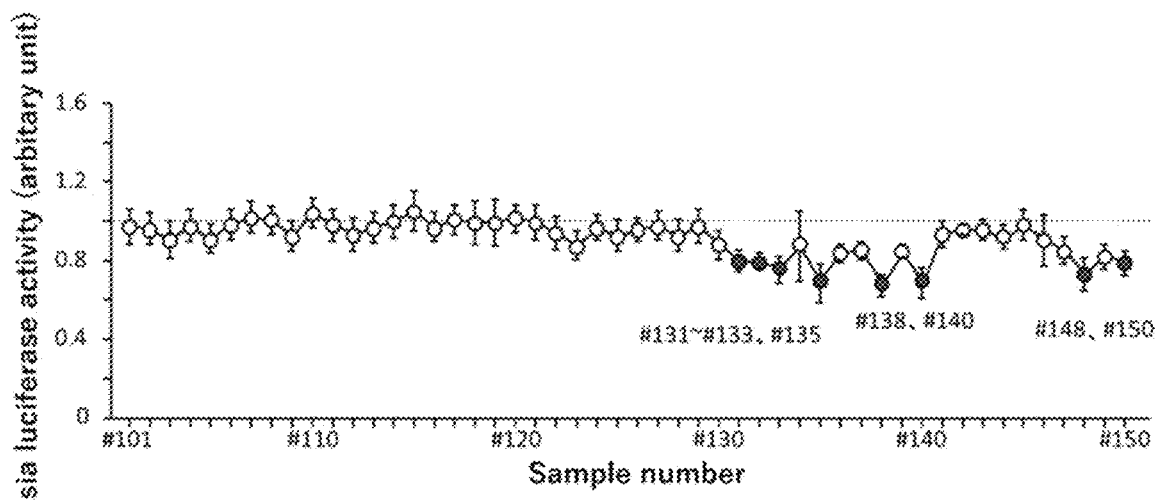
FIG. 14 It is a figure showing the results of measuring the relative activity value of Gaussia luciferase activity with respect to the blank in the primary screening of tripeptides in the tripeptide library (#101-#150) assumed from the amino acid sequence of α-8S globulin. The relative activity value of each sample is indicated by a circle, and a black circle indicates a sample showing a significantly lower value than the blank.
Figure 15:
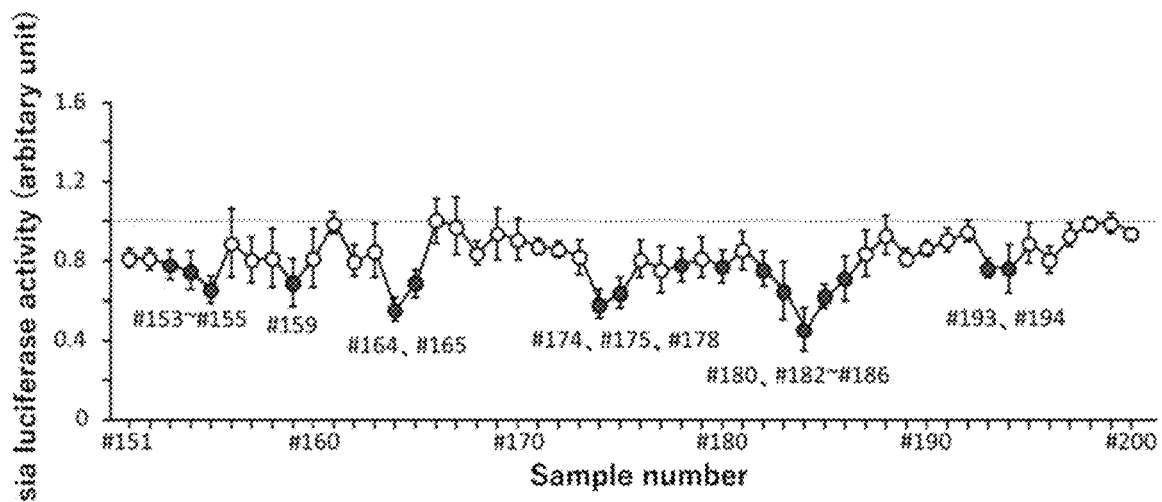
FIG. 15 It is a figure showing the results of measuring the relative activity value of Gaussia luciferase activity with respect to the blank in the primary screening of tripeptides in the tripeptide library (#151-#200) assumed from the amino acid sequence of α-8S globulin. The relative activity value of each sample is indicated by a circle, and a black circle indicates a sample showing a significantly lower value than the blank.
Figure 16:
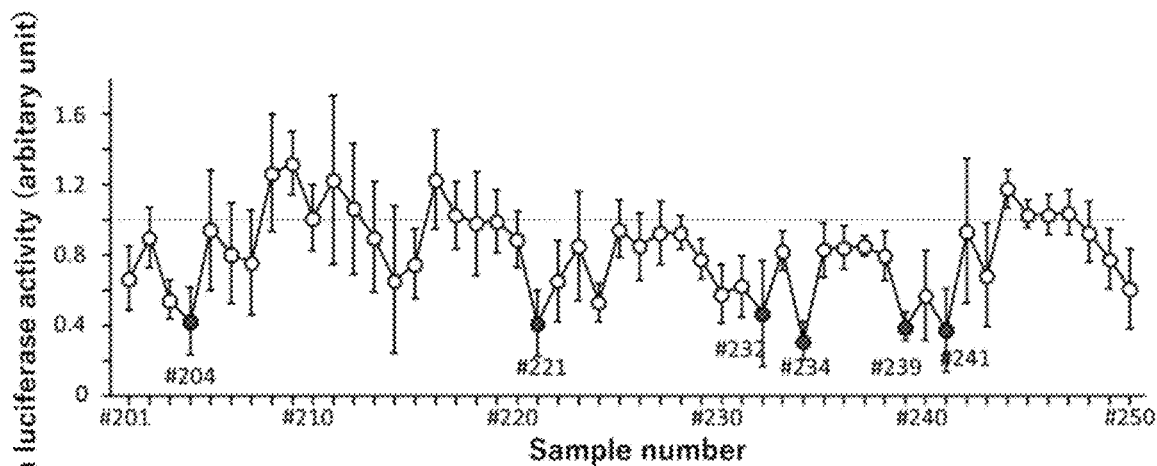
FIG. 16 It is a figure showing the results of measuring the relative activity value of Gaussia luciferase activity with respect to the blank in the primary screening of tripeptides in the tripeptide library (#201-#250) assumed from the amino acid sequence of α-8S globulin. The relative activity value of each sample is indicated by a circle, and a black circle indicates a sample showing a significantly lower value than the blank.
Figure 17:
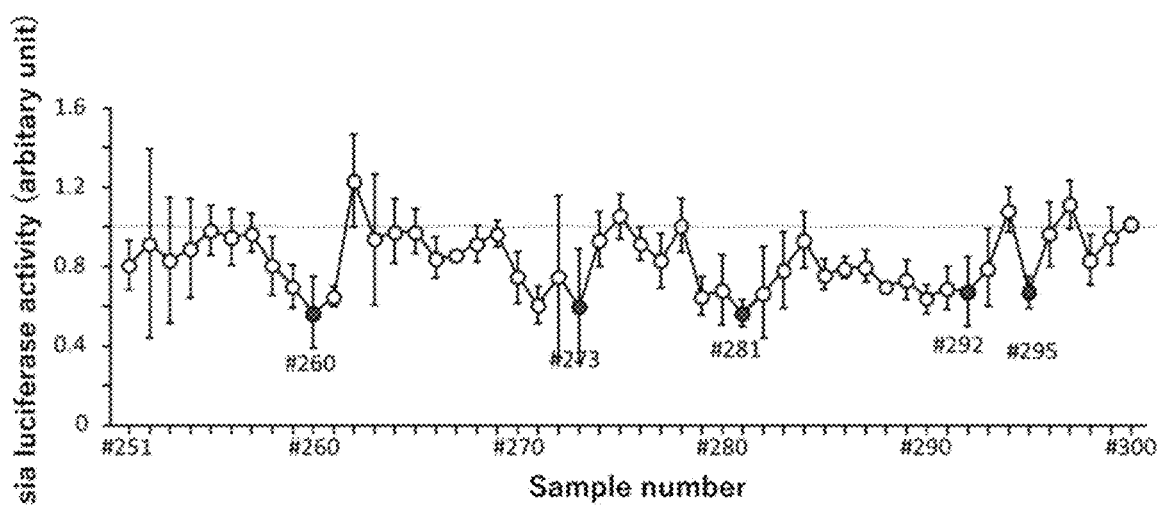
FIG. 17 It is a figure showing the results of measuring the relative activity value of Gaussia luciferase activity with respect to the blank in the primary screening of tripeptides in the tripeptide library (#251-#300) assumed from the amino acid sequence of α-8S globulin. The relative activity value of each sample is indicated by a circle, and a black circle indicates a sample showing a significantly lower value than the blank.
Figure 18:
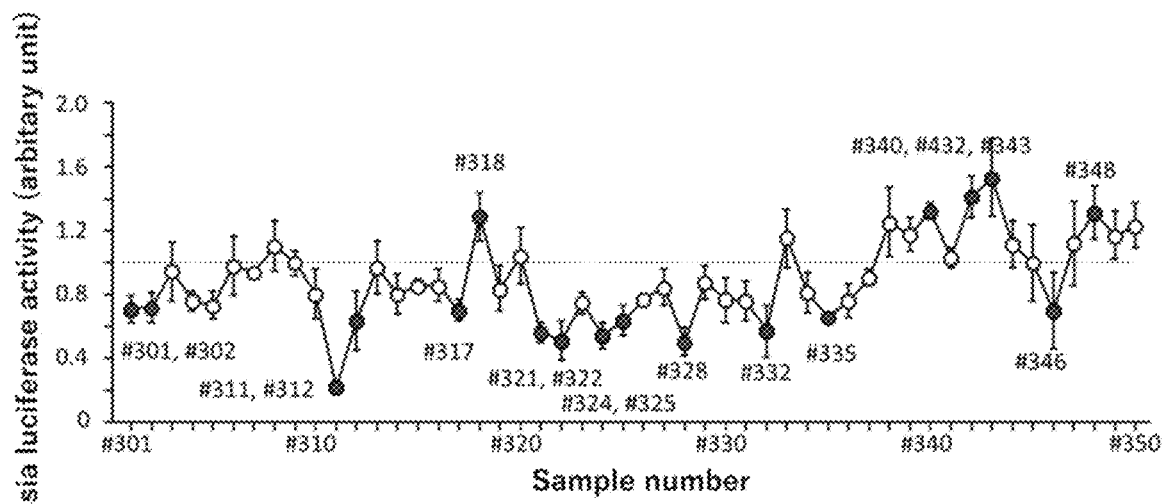
FIG. 18 It is a figure showing the results of measuring the relative activity value of Gaussia luciferase activity with respect to the blank in the primary screening of tripeptides in the tripeptide library (#301-#350) assumed from the amino acid sequence of α-8S globulin. The relative activity value of each sample is indicated by a circle, and a black circle indicates a sample showing a significantly lower value than the blank.
Figure 19:
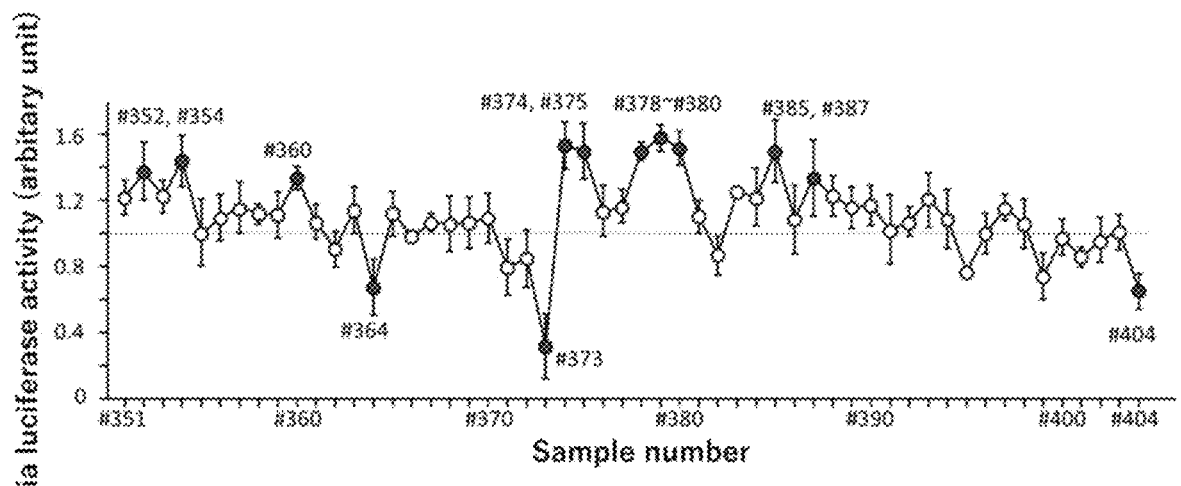
FIG. 19 It is a figure showing the results of measuring the relative activity value of Gaussia luciferase activity with respect to the blank in the primary screening of tripeptides in the tripeptide library (#351-#404) assumed from the amino acid sequence of α-8S globulin. The relative activity value of each sample is indicated by a circle, and a black circle indicates a sample showing a significantly lower value than the blank.

The 13 dipeptides showing the effect of suppressing Fasn gene expression in the secondary screening were evaluated by the method according to the above-described "(Tertiary Screening Method)". The results are shown in FIGS. 10 and 11.

Among the 13 dipeptides, 11 dipeptides, Ala-Gly, His-Asn, His-Ser, His-Thr, His-Trp, Val-Met, Trp-Glu, Trp-Lys, Tyr-Lys, Tyr-Ser and Tyr-Tyr, significantly suppressed the expression of the Fasn gene with respect to the control. From the results, an effect of suppressing hepatic lipogenesis was confirmed in the 11 dipeptides, Ala-Gly, His-Asn, His-Ser, His-Thr, His-Trp, Val-Met, Trp-Glu, Trp-Lys, Tyr-Lys, Tyr-Ser or Tyr-Tyr.

Examples 2 to 3: Tripeptides

Tripeptides which may be involved in an effect of suppressing hepatic lipogenesis were screened from 587 tripeptides library including 404 tripeptides library assumed from amino acid sequence of α-8S globulin which is major content of mung bean protein and 183 tripeptides library assumed from amino acid sequence of α'/β-8S globulin. The above-described 587 tripeitdes were synthesized by peptide synthesizer (ResPep SL (INTAVIS Bioanalytical Instruments AG)).

Example 2: Study of 404 Tripeptides Library Assumed from Amino Acid Sequence of α-8S Globulin (Primary Screening)

Screening 404 tripeptides library assumed from amino acid sequence of α-8S globulin was carried out according to the method of the above-mentioned "(Primary Screening Method)". The results are shown in FIGS. 12 to 19.

Statistically, 68 tripeptides were confirmed as having an activity of suppressing Gaussia luciferase activity (FIGS. 12 to 19, Table 2).

TABLE 2

68 tripeptides confirmed to be effective in primary screening

| Tri-peptide library No. | Tri-peptide |
|---|---|
| #003 | Val-Ile-Leu(VIL) |
| #032 | Gly-Ser-Leu(GSL) |
| #042 | Ser-Leu-Leu(SLL) |
| #044 | Leu-Asp-Met(LDM) |
| #053 | Glu-Ile-Pro(EIP) |
| #068 | Ala-Gln-Pro(AQP) |
| #075 | Lys-Gly-Pro(KGP) |
| #077 | Tyr-Leu-Gln(YLQ) |
| #078 | Ser-Gln-Gln(SQQ) |
| #079 | Glu-Gln-Gln(EQQ) |
| #082 | Val-Leu-Gln(VLQ) |
| #083 | His-Ala-Gln(HAQ) |
| #086 | Gln-Lys-Gln(QKQ) |
| #131 | Asp-Val-Thr(DVT) |
| #132 | Ala-Glu-Val(AEV) |
| #133 | Val-Ser-Val(VSV) |
| #135 | Arg-Ala-Val(RAV) |
| #138 | Leu-Ala-Val(LAV) |
| #140 | Glu-Gly-Val(EGV) |
| #148 | Pro-Ala-Gly(PAG) |
| #150 | Ala-Phe-Gly(AFG) |
| #153 | Leu-Arg-Ile(LRI) |
| #154 | Gly-Val-Ile(GVI) |
| #155 | Lys-Ala-Ile(KAI) |
| #159 | Lys-Leu-Gly(KLG) |
| #164 | Glu-Gln-Ile(EQI) |
| #165 | Ile-Val-Ile(IVI) |
| #174 | Lys-Pro-Ile(KPI) |
| #175 | Leu-Val-Ile(LVI) |
| #177 | Pro-Asp-Gly(PDG) |
| #178 | Glu-Glu-Gly(EEG) |
| #180 | Arg-Lys-Gly(RKG) |
| #182 | Ser-Asn-Ile(SNI) |
| #183 | Ser-Asp-Ile(SDI) |
| #184 | Phe-Glu-Ile(FEI) |
| #185 | Ala-Asn-Ile(ANI) |
| #186 | Gly-Pro-Phe(GPF) |
| #193 | Lys-Glu-Ile(KEI) |
| #194 | Met-Phe-Ile(MFI) |
| #204 | Asn-Ile-Leu(NIL) |
| #221 | Gly-Gly-Lys(GGK) |
| #224 | Phe-Gly-Ile(FGI) |
| #232 | Ala-Val-Leu(AVL) |
| #234 | Met-Ser-Lys(MSK) |
| #239 | Gly-His-Leu(GHL) |
| #241 | Leu-Thr-Leu(LTL) |
| #260 | Val-Asp-Ala(VDA) |
| #273 | Leu-Arg-Asp(LRD) |
| #281 | Asn-Leu-Glu(NLE) |
| #292 | Lys-Arg-Glu(KRE) |
| #295 | Trp-Phe-Glu(WFE) |
| #301 | Gln-Gln-Glu(QQE) |
| #302 | Gln-Glu-Glu(QEE) |
| #311 | Ser-Gly-Glu(SGE) |
| #312 | Gln-Ser-Glu(QSE) |
| #317 | Phe-Tyr-Phe(FYF) |
| #318 | Arg-Trp-Phe(RWF) |
| #321 | Glu-Arg-Phe(QRF) |
| #322 | Val-Glu-Phe(VEF) |
| #324 | Thr-Thr-Phe(TTF) |
| #325 | Thr-Phe-Phe(TFF) |
| #328 | Asp-Phe-Phe(DFF) |
| #332 | Gln-Pro-Phe(QPF) |
| #335 | Asp-Val-Phe(DVF) |
| #346 | Pro-Phe-Tyr(PFY) |
| #364 | Phe-Ile-Arg(FIR) |
| #373 | Asn-Gly-Arg(NGR) |
| #404 | Ile-Ile-Pro(IIP) |

(Secondary Screening)

Tripepitdes shown in Table 2 were synthesized by peptide synthesizer (ResPep SL (INTAVIS Bioanalytical Instruments AG)). The synthesized tripeptides were evaluated by the method according to the above-described "(Secondary Screening Method)". The results are shown in FIGS. 20 and 21.

Figure 20:
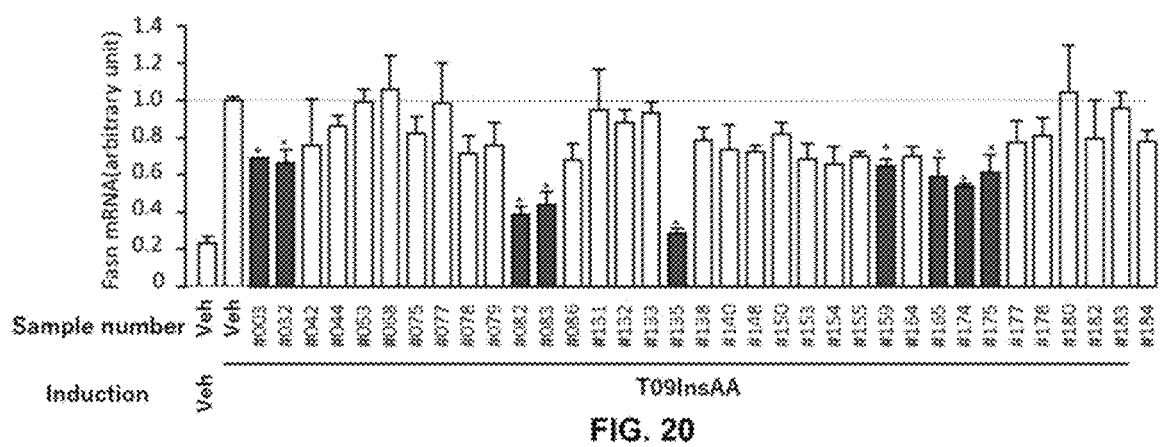
FIG. 20 It is a figure showing the results of measuring the Fasn gene expression level in the secondary screening of 35 tripeptides in the study of tripeptides assumed from the amino acid sequence of α-8S globulin. The black bar graph shows a sample in which the Fasn gene expression level was significantly reduced as compared to the blank (described as Veh).
Figure 21:
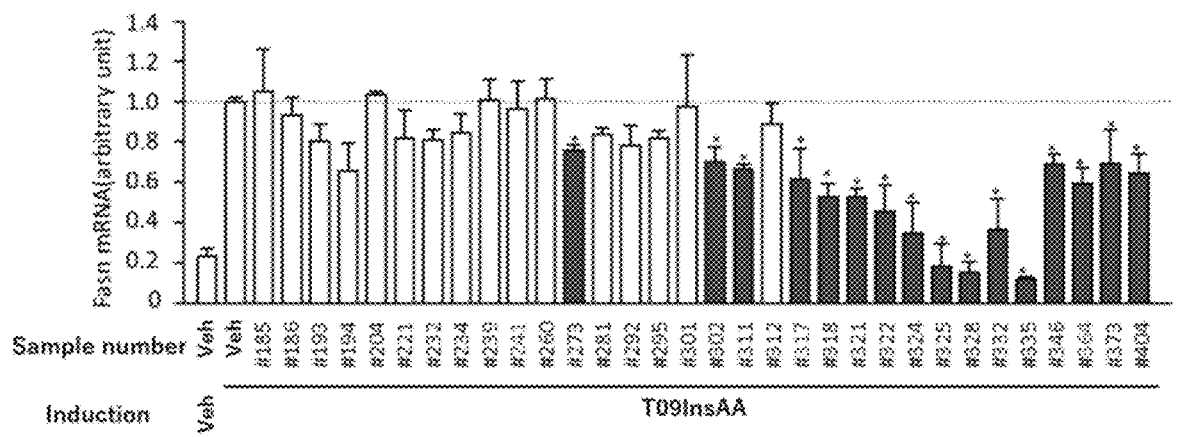
FIG. 21 It is a figure showing the results of measuring the Fasn gene expression level in the secondary screening of 32 tripeptides in the study of tripeptides assumed from the amino acid sequence of α-8S globulin. The black bar graph shows a sample in which the Fasn gene expression level was significantly reduced as compared to the blank (described as Veh).

Among the 68 tripeptides, 25 tripeptides significantly suppressed the expression of the Fasn gene with respect to the control (FIGS. 20 and 21, Table 3).

TABLE 3

25 tripeptides confirmed to be effective in the secondary screening

| Tri-peptide library No. | Tri-peptide |
| --- | --- |
| #003 | Val-Ile-Leu(VIL) |
| #032 | Gly-Ser-Leu(GSL) |
| #082 | Val-Leu-Gln(VLQ) |
| #083 | His-Ala-Gln(HAQ) |
| #135 | Arg-Ala-Val(RAV) |
| #159 | Lys-Leu-Gly(KLG) |
| #165 | Ile-Val-Ile(IVI) |
| #174 | Lys-Pro-Ile(KPI) |
| #175 | Leu-Val-Ile(LVI) |
| #273 | Leu-Arg-Asp(LRD) |
| #302 | Gln-Glu-Glu(QEE) |
| #311 | Ser-Gly-Glu(SGE) |
| #317 | Phe-Tyr-Phe(FYF) |
| #318 | Arg-Trp-Phe(RWF) |
| #321 | Glu-Arg-Phe(QRF) |
| #322 | Val-Glu-Phe(VEF) |
| #324 | Thr-Thr-Phe(TTF) |
| #325 | Thr-Phe-Phe(TFF) |
| #328 | Asp-Phe-Phe(DFF) |
| #332 | Gln-Pro-Phe(QPF) |
| #335 | Asp-Val-Phe(DVF) |
| #346 | Pro-Phe-Tyr(PFY) |
| #364 | Phe-Ile-Arg(FIR) |
| #373 | Asn-Gly-Arg(NGR) |
| #404 | Ile-Ile-Pro(IIP) |

(Tertiary Screening)

Figure 22:
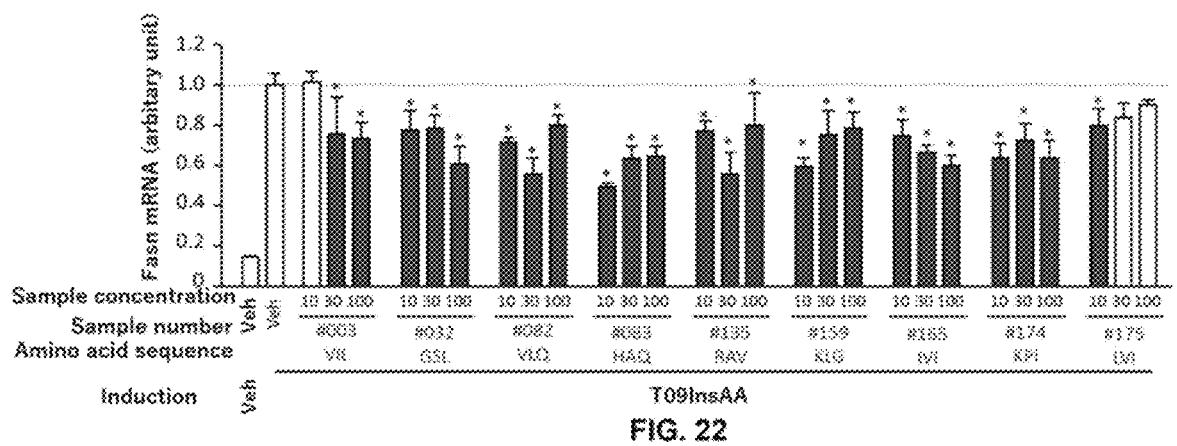
FIG. 22 It is a figure showing the results of measuring the Fasn gene expression level in the tertiary screening of 9 tripeptides in the study of tripeptides assumed from the amino acid sequence of α-8S globulin. The black bar graph shows a sample in which the Fasn gene expression level was significantly reduced as compared to the blank (described as Veh).
Figure 23:
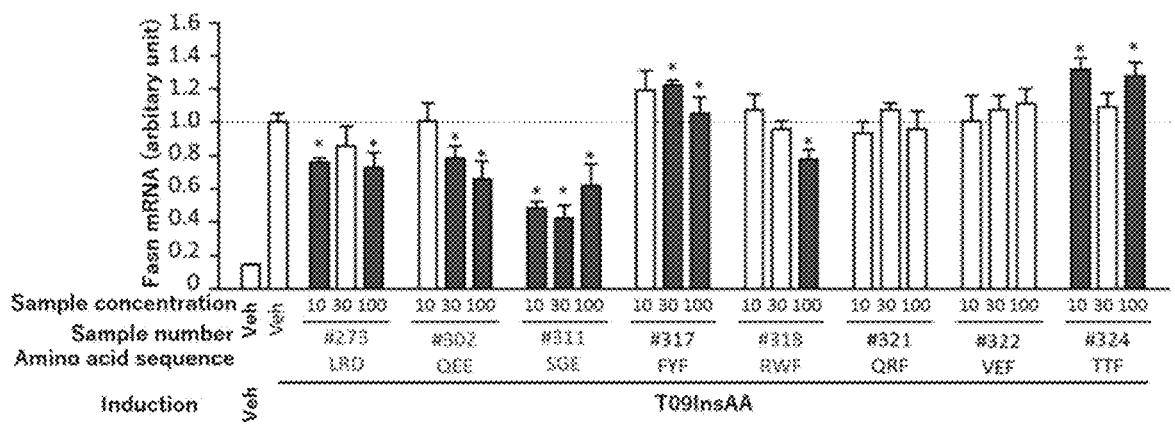
FIG. 23 It is a figure showing the results of measuring the Fasn gene expression level in the tertiary screening of 8 tripeptides in the study of tripeptides assumed from the amino acid sequence of α-8S globulin. The black bar graph shows a sample in which the Fasn gene expression level was significantly reduced as compared to the blank (described as Veh).
Figure 24:
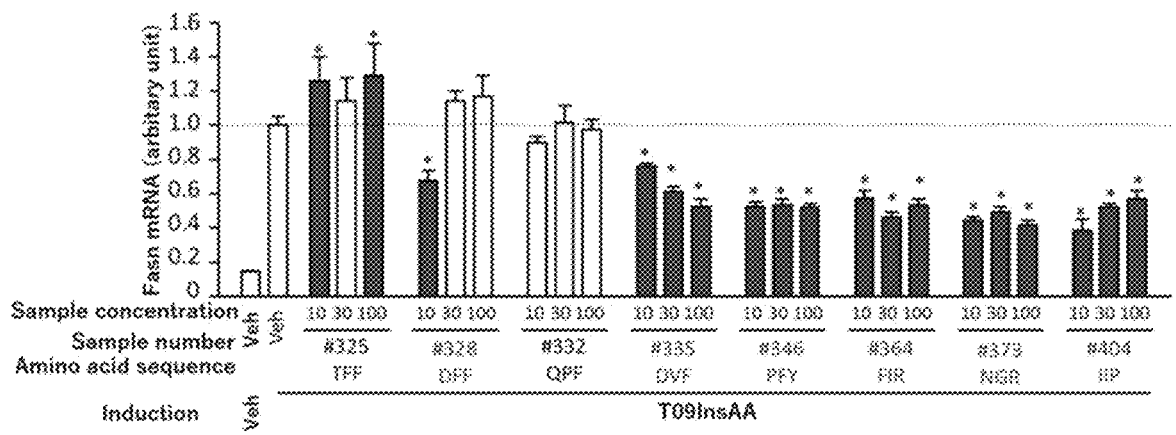
FIG. 24 It is a figure showing the results of measuring the Fasn gene expression level in the tertiary screening of 8 tripeptides in the study of tripeptides assumed from the amino acid sequence of α-8S globulin. The black bar graph shows a sample in which the Fasn gene expression level was significantly reduced as compared to the blank (described as Veh).
Figure 25:
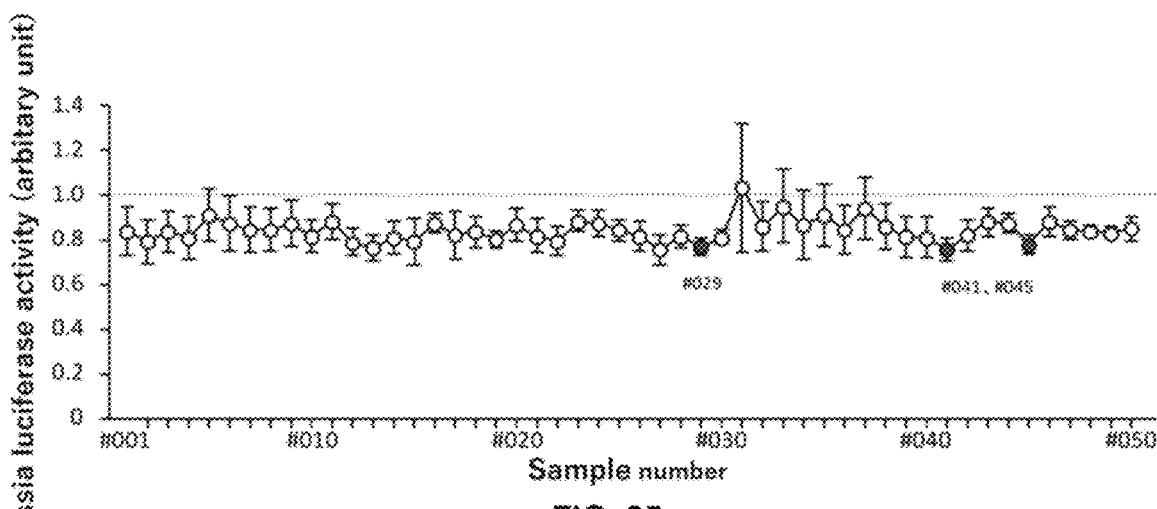
FIG. 25 It is a figure showing the results of measuring the relative activity value of Gaussia luciferase activity with respect to the blank in the primary screening of tripeptides in the tripeptide library (#1-#50) assumed from the amino acid sequence of α'/β-8S globulin. The relative activity value of each sample is indicated by a circle, and a black circle indicates a sample showing a significantly lower value than the blank.
Figure 26:
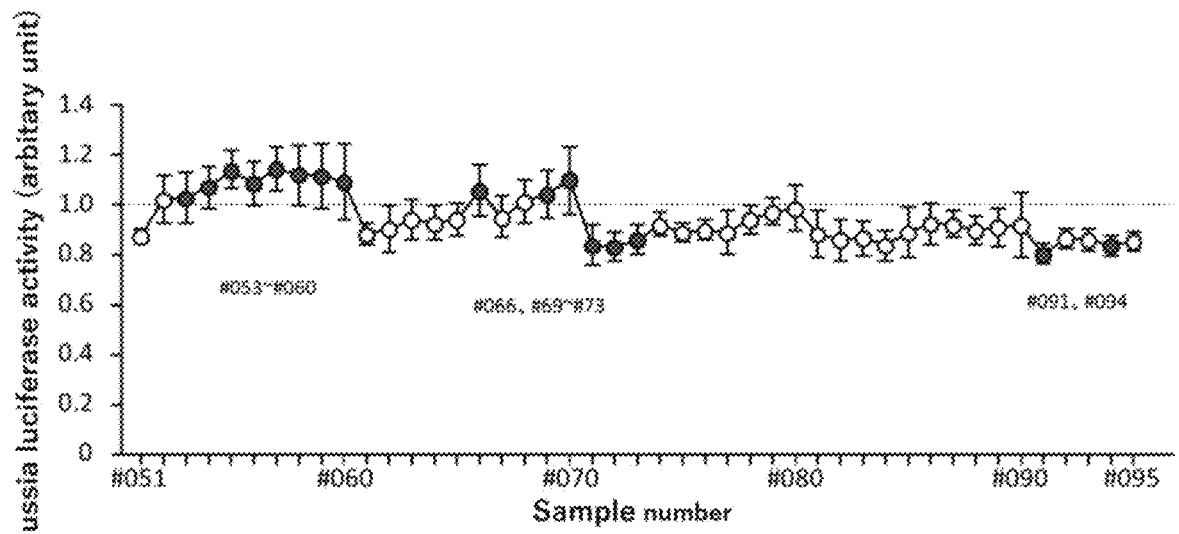
FIG. 26 It is a figure showing the results of measuring the relative activity value of Gaussia luciferase activity with respect to the blank in the primary screening of tripeptides in the tripeptide library (#51-#95) assumed from the amino acid sequence of α'/β-8S globulin. The relative activity value of each sample is indicated by a circle, and a black circle indicates a sample showing a significantly lower value than the blank.
Figure 27:
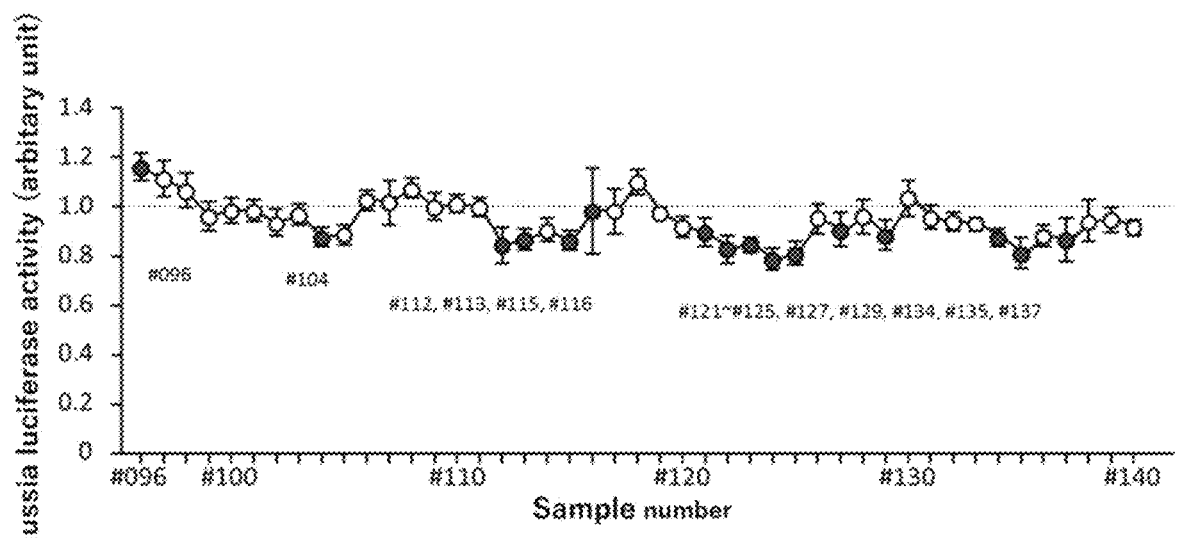
FIG. 27 It is a figure showing the results of measuring the relative activity value of Gaussia luciferase activity with respect to the blank in the primary screening of tripeptides in the tripeptide library (#96-#140) assumed from the amino acid sequence of α'/β-8S globulin. The relative activity value of each sample is indicated by a circle, and a black circle indicates a sample showing a significantly lower value than the blank.
Figure 28:
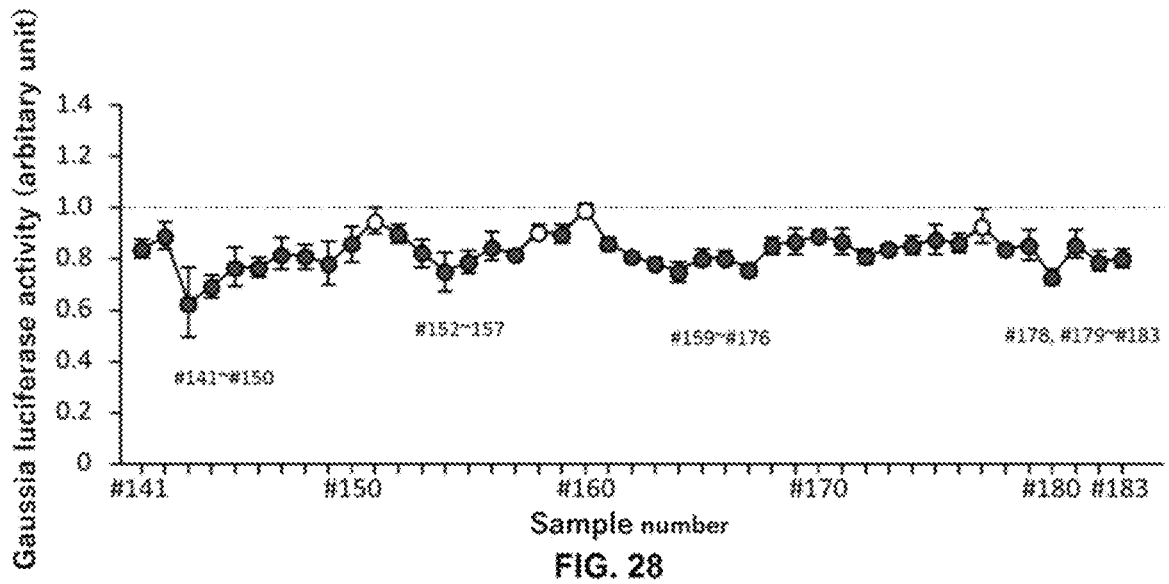
FIG. 28 It is a figure showing the results of measuring the relative activity value of Gaussia luciferase activity with respect to the blank in the primary screening of tripeptides in the tripeptide library (#141-#183) assumed from the amino acid sequence of α'/β-8S globulin. The relative activity value of each sample is indicated by a circle, and a black circle indicates a sample showing a significantly lower value than the blank.

The 25 tripeptides showing the effect of suppressing Fasn gene expression in the secondary screening were evaluated by the method according to the above-described "(Tertiary Screening Method)". The results are shown in FIGS. 22 to 24.

Among the 25 tripeptides, 19 tripeptides, Val-Ile-Leu, Gly-Ser-Leu, Val-Leu-Gln, His-Ala-Gln, Arg-Ala-Val, Lys-Leu-Gly, Ile-Val-Ile, Lys-Pro-Ile, Leu-Val-Ile, Leu-Arg-Asp, Gln-Glu-Glu, Ser-Gly-Glu, Arg-Trp-Phe, Asp-Phe-Phe, Asp-Val-Phe, Pro-Phe-Tyr, Phe-Ile-Arg, Asn-Gly-Arg and Ile-Ile-Pro, significantly suppressed the expression of the Fasn gene with respect to the control.

Example 3: Study of 183 Tripeptides Library Assumed from Amino Acid Sequence of α'/β-8S Globulin (Primary Screening)

Screening 183 tripeptides library assumed from amino acid sequence of α'/β-8S globulin was carried out according to the method of the above-mentioned "(Primary Screening Method)". The results are shown in FIGS. 25 to 28.

Statistically, 62 tripeptides were confirmed as having an activity of suppressing Gaussia luciferase activity (FIGS. 25 to 28, Table 4).

TABLE 4

| Tri-peptide library No. | Tri-peptide |
| --- | --- |
| #029 | Ser-Leu-Glu(SLE) |
| #041 | Arg-Gly-Phe(RGF) |
| #045 | Ala-Pro-Gly(APG) |
| #071 | Asp-Pro-Ile(NPI) |
| #072 | Arg-Ala-Ile(RAI) |
| #073 | Arg-Val-Ile(RVI) |
| #091 | Val-Glu-Lys(VEK) |
| #094 | Asp-Asn-Leu(DNL) |
| #104 | Ser-Ile-Leu(SIL) |
| #112 | Gly-Gln-Asn(GQN) |
| #113 | Ile-Gln-Asn(IQN) |
| #115 | Asn-Asp-Asn(NDN) |
| #116 | Asn-Pro-Asn(NPN) |
| #121 | Ala-Ile-Pro(AIP) |
| #122 | Ala-Tyr-Pro(AYP) |
| #123 | Asp-Glu-Pro(DEP) |
| #124 | Glu-Gly-Pro(EGP) |
| #125 | Pro-Ala-Pro(PAP) |
| #127 | Ser-Asn-Pro(SNP) |
| #129 | Val-Ile-Pro(VIP) |
| #134 | Gln-Ile-Gln(QIQ) |
| #135 | Arg-Ser-Gln(RSQ) |
| #137 | Ser-Asp-Gln(SDQ) |
| #141 | Phe-Gly-Arg(FGR) |
| #142 | Gly-Gly-Arg(GGR) |
| #143 | Gly-Leu-Arg(GLR) |
| #144 | Ile-Asp-Arg(IDR) |
| #145 | Ile-His-Arg(IHR) |
| #146 | Ile-Asn-Arg(INR) |
| #147 | Lys-Gly-Arg(KGR) |
| #148 | Gln-Gln-Arg(QQR) |
| #149 | Ser-Ser-Arg(SSR) |
| #150 | Trp-Phe-Arg(WFR) |
| #152 | Asp-Glu-Ser(DES) |
| #153 | Asp-Val-Ser(DVS) |
| #154 | Phe-Ile-Ser(FIS) |
| #155 | Phe-Lys-Ser(FKS) |
| #156 | Phe-Gln-Ser(FQS) |
| #157 | Gly-Pro-Ser(GPS) |
| #159 | Lys-Gly-Ser(KGS) |
| #161 | Arg-Asn-Ser(RNS) |
| #162 | Ser-Asp-Ser(SDS) |
| #163 | Ser-Thr-Ser(STS) |
| #164 | Val-Met-Ser(VMS) |
| #165 | Phe-Arg-Thr(FRT) |
| #166 | Ile-Leu-Thr(ILT) |
| #167 | Gln-Ser-Thr(QST) |
| #168 | Asp-Arg-Val(DRV) |
| #169 | His-Phe-Val(HFV) |
| #170 | Ile-Pro-Val(IPV) |
| #171 | Lys-Leu-Val(KLV) |
| #172 | Leu-Glu-Val(LEV) |
| #173 | Asn-Lys-Val(NKV) |
| #174 | Asn-Arg-Val(NRV) |
| #175 | Ser-Ser-Val(SSV) |
| #176 | Val-Phe-Val(VFV) |
| #178 | Asp-Ser-Tyr(DSY) |
| #179 | Glu-Phe-Tyr(EFY) |
| #180 | Asn-Gln-Tyr(NQY) |
| #181 | Arg-Trp-Tyr(RWY) |
| #182 | Ser-Leu-Tyr(SLY) |
| #183 | Ser-Asp-Phe(SDF) |

(Secondary Screening)

Tripepitdes shown in Table 4 were synthesized by peptide synthesizer (ResPep SL (INTAVIS Bioanalytical Instruments AG)). The synthesized tripeptides were evaluated by the method according to the above-described "(Secondary Screening Method)". The results are shown in FIGS. 29 and 30.

Figure 29:
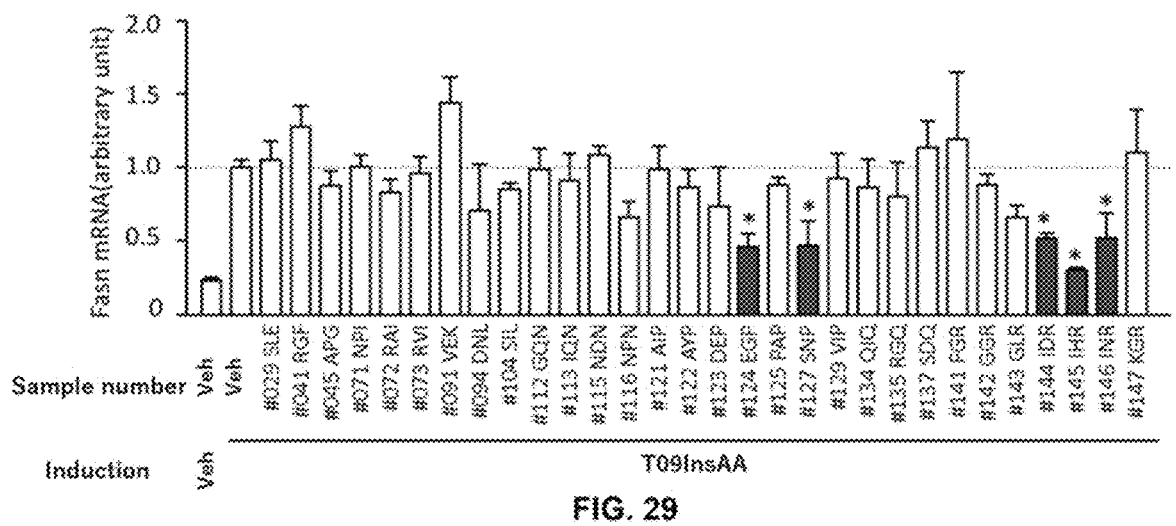
FIG. 29 It is a figure showing the results of measuring the Fasn gene expression level in the secondary screening of 30 tripeptides in the study of tripeptides assumed from the amino acid sequence of α'/β-8S globulin. The black bar graph shows a sample in which the Fasn gene expression level was significantly reduced as compared to the blank (described as Veh).
Figure 30:
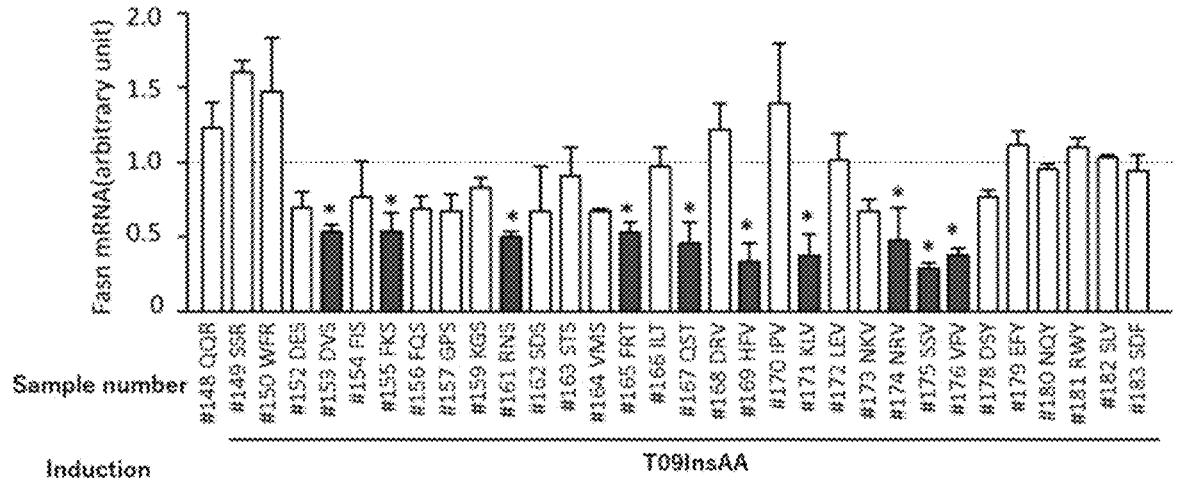
FIG. 30 It is a figure showing the results of measuring the Fasn gene expression level in the secondary screening of 32 tripeptides in the study of tripeptides assumed from the amino acid sequence of α'/β-8S globulin. The black bar graph shows a sample in which the Fasn gene expression level was significantly reduced as compared to the blank (described as Veh).

Among the 62 tripeptides, 15 tripeptides significantly suppressed the expression of the Fasn gene with respect to the control (FIGS. 29 and 30, Table 5).

TABLE 5

| Tri-peptide library No. | Tri-peptide |
|---|---|
| #124 | Glu-Gly-Pro(EGP) |
| #127 | Ser-Asn-Pro(SNP) |
| #144 | Ile-Asp-Arg(IDR) |
| #145 | Ile-His-Arg(IHR) |
| #146 | Ile-Asn-Arg(INR) |
| #153 | Asp-Val-Ser(DVS) |
| #155 | Phe-Lys-Ser(FKS) |
| #161 | Arg-Asn-Ser(RNS) |
| #165 | Phe-Arg-Thr(FRT) |
| #167 | Gln-Ser-Thr(QST) |
| #169 | His-Phe-Val(HFV) |
| #171 | Lys-Leu-Val(KLV) |
| #174 | Asn-Arg-Val(NRV) |
| #175 | Ser-Ser-Val(SSV) |
| #176 | Val-Phe-Val(VFV) |

(Tertiary Screening)

Figure 31:
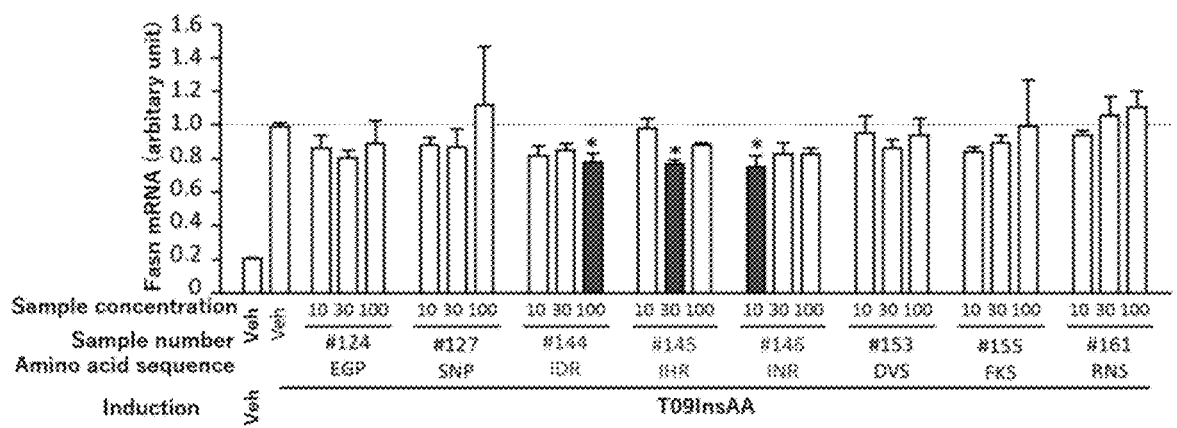
FIG. 31 It is a figure showing the results of measuring the Fasn gene expression level in the tertiary screening of 8 tripeptides in the study of tripeptides assumed from the amino acid sequence of α'/β-8S globulin. The black bar graph shows a sample in which the Fasn gene expression level was significantly reduced as compared to the blank (described as Veh).
Figure 32:
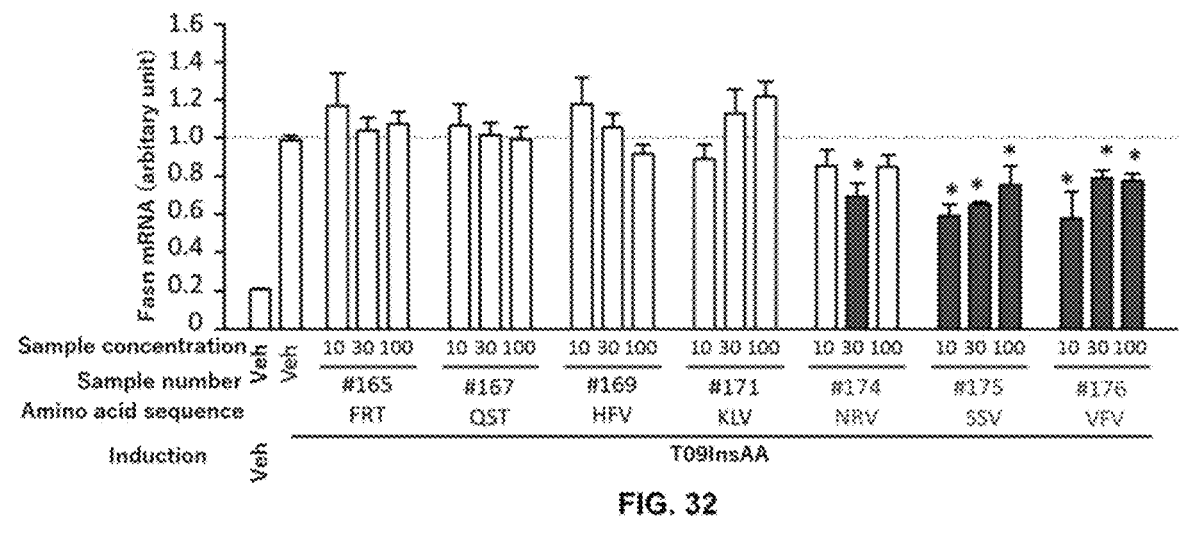

The 15 tripeptides showing the effect of suppressing Fasn gene expression in the secondary screening were evaluated by the method according to the above-described "(Tertiary Screening Method)". The results are shown in FIGS. 31 and 32.

Among the 15 tripeptides, 6 tripeptides, Ile-Asp-Arg, Ile-His-Arg, Ile-Asp-Arg, Asn-Arg-Val, Ser-Ser-Val and Val-Phe-Val, significantly suppressed the expression of the Fasn gene with respect to the control.

As shown in the above, from the results of study of 404 tripeptides library assumed from amino acid sequence of α-8S globulin and 183 tripeptides library assumed from amino acid sequence of α'/β-8S globulin, an effect of suppressing hepatic lipogenesis was confirmed in the 25 tripeptides, Val-Ile-Leu, Gly-Ser-Leu, Val-Leu-Gln, His-Ala-Gln, Arg-Ala-Val, Lys-Leu-Gly, Ile-Val-Ile, Lys-Pro-Ile, Leu-Val-Ile, Leu-Arg-Asp, Gln-Glu-Glu, Ser-Gly-Glu, Arg-Trp-Phe, Asp-Phe-Phe, Asp-Val-Phe, Pro-Phe-Tyr, Phe-Ile-Arg, Asn-Gly-Arg, Ile-Ile-Pro, Ile-Asp-Arg, Ile-His-Arg, Ile-Asp-Arg, Asn-Arg-Val, Ser-Ser-Val or Val-Phe-Val.

The invention claimed is:

1. A method for suppressing hepatic lipogenesis in a subject in need thereof, comprising administering to the subject an agent for suppressing hepatic lipogenesis comprising one or more peptide selected from the group consisting of His-Asn, His-Ser, His-Thr, His-Trp, Trp-Glu, Trp-Lys, Tyr-Lys, Tyr-Ser, and Tyr-Tyr, as an active ingredient.

2. The method according to claim 1, wherein the peptide as an active ingredient is one or more dipeptide selected from the group consisting of His-Asn, His-Ser, His-Thr, His-Trp, Tyr-Lys, Tyr-Ser and Tyr-Tyr.

3. The method according to claim 1, wherein the peptide as an active ingredient is one or more dipeptide selected from the group consisting of His-Asn, His-Ser, His-Thr, His-Trp, Trp-Glu, and Trp-Lys.

4. The method according to claim 1, wherein the peptide as an active ingredient is one or more dipeptide selected from the group consisting of His-Asn, His-Ser, His-Thr, and His-Trp.

* * * * *